US012391651B2

(12) United States Patent
Lee et al.

(10) Patent No.: US 12,391,651 B2
(45) Date of Patent: Aug. 19, 2025

(54) ORGANIC ELECTROLUMINESCENT COMPOUND AND ORGANIC ELECTROLUMINESCENT DEVICE COMPRISING THE SAME

(71) Applicant: ROHM AND HAAS ELECTRONIC MATERIALS KOREA LTD., Chungcheongnam-do (KR)

(72) Inventors: Hyo-Jung Lee, Gyeonggi-do (KR); Mi-Ja Lee, Gyeonggi-do (KR); Dong-Hyung Lee, Gyeonggi-do (KR); Jin-Ri Hong, Gyeonggi-do (KR)

(73) Assignee: DuPont Specialty Materials Korea Ltd. (KR)

( * ) Notice: Subject to any disclaimer, the term of this patent is extended or adjusted under 35 U.S.C. 154(b) by 840 days.

(21) Appl. No.: 17/175,105

(22) Filed: Feb. 12, 2021

(65) Prior Publication Data

US 2021/0269405 A1   Sep. 2, 2021

(30) Foreign Application Priority Data

Feb. 25, 2020   (KR) ........................ 10-2020-0023139

(51) Int. Cl.
| | |
|---|---|
| *C07D 223/32* | (2006.01) |
| *H10K 50/15* | (2023.01) |
| *H10K 50/16* | (2023.01) |
| *H10K 50/17* | (2023.01) |
| *H10K 85/30* | (2023.01) |
| *H10K 85/60* | (2023.01) |

(52) U.S. Cl.
CPC .......... *C07D 223/32* (2013.01); *H10K 85/30* (2023.02); *H10K 85/615* (2023.02); *H10K 85/633* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02)

(58) Field of Classification Search
CPC ............. H01K 85/615; H01K 85/6572; H01K 85/6574; H01K 85/6576
See application file for complete search history.

(56) References Cited

U.S. PATENT DOCUMENTS

| | | | | |
|---|---|---|---|---|
| 2005/0233165 A1* | 10/2005 | Ido | ........................ | C07C 13/567 |
| | | | | 428/917 |
| 2009/0321729 A1 | 12/2009 | Ido et al. | | |
| 2018/0006244 A1* | 1/2018 | Cha | ...................... | C07D 493/10 |
| 2018/0123055 A1* | 5/2018 | Park | ...................... | C07D 307/93 |
| 2018/0301629 A1* | 10/2018 | Hatakeyama | ........ | H10K 85/657 |
| 2019/0312212 A1 | 10/2019 | Moon et al. | | |
| 2020/0013964 A1 | 1/2020 | Lee et al. | | |
| 2020/0013965 A1 | 1/2020 | Yang et al. | | |
| 2021/0013418 A1* | 1/2021 | Kim | ........................ | C07C 13/62 |
| 2021/0135127 A1* | 5/2021 | Jung | .................. | H10K 85/6574 |
| 2021/0296595 A1* | 9/2021 | Cho | .................... | H10K 85/6576 |
| 2022/0006019 A1* | 1/2022 | Kim | ...................... | H10K 85/626 |
| 2022/0123223 A1* | 4/2022 | Kang | .................. | H10K 85/6574 |
| 2022/0231228 A1* | 7/2022 | Lee | ....................... | H10K 85/624 |
| 2022/0263031 A1* | 8/2022 | Um | ........................ | C09K 11/02 |
| 2023/0006147 A1* | 1/2023 | Cho | ...................... | H10K 85/141 |
| 2023/0141435 A1* | 5/2023 | Jung | .................... | H10K 85/633 |
| | | | | 257/40 |

FOREIGN PATENT DOCUMENTS

| | | | |
|---|---|---|---|
| KR | 20160107669 A | 9/2016 | |
| WO | WO-2020262853 A1 * | 12/2020 | ........... C07D 493/12 |

OTHER PUBLICATIONS

Machine translation of WO-2020262853-A1, 2024 (Year: 2024).*
Request for the Submission of an Opinion issued from Korean Intellectual Property Office for Korea Patent application No. 10-2020-0023139; Application Date: Feb. 25, 2020.
Cited Reference from Japan Patent Office for Japan patent application No. 2021-019167; Application Date Feb. 9, 2021.

* cited by examiner

*Primary Examiner* — Liam J Heincer
(74) *Attorney, Agent, or Firm* — G. Creston Campbell

(57) ABSTRACT

The present disclosure relates to an organic electroluminescent compound, and an organic electroluminescent device comprising the same. By comprising the organic electroluminescent compound of the present disclosure, it is possible to provide an organic electroluminescent device having improved driving voltage, lifetime properties, and/or power efficiency.

7 Claims, No Drawings

ORGANIC ELECTROLUMINESCENT COMPOUND AND ORGANIC ELECTROLUMINESCENT DEVICE COMPRISING THE SAME

TECHNICAL FIELD

The present disclosure relates to an organic electroluminescent compound and an organic electroluminescent device comprising the same.

BACKGROUND ART

A small molecular green organic electroluminescent device (OLED) was first developed by Tang, et al., of Eastman Kodak in 1987 by using TPD/ALq3 bi-layer consisting of a light-emitting layer and a charge transport layer. Thereafter, the development of OLEDs was rapidly effected and OLEDs have been commercialized. At present, OLEDs primarily use phosphorescent materials having excellent luminous efficiency in panel implementation. Low driving voltage and high luminous efficiency are required for long-time use and high resolution of a display.

In order to enhance luminous efficiency, driving voltage, and/or lifetime properties, various materials or concepts for an organic layer of an organic electroluminescent device have been proposed. However, they were not satisfactory in practical use.

DISCLOSURE OF INVENTION

Technical Problem

The objective of the present disclosure is to provide an organic electroluminescent compound which is efficient in producing an organic electroluminescent device having improved driving voltage, lifetime properties, and/or power efficiency. Another objective of the present disclosure is to provide an organic electroluminescent device comprising the organic electroluminescent compound.

Solution to Problem

The present inventors have found that the above objective can be achieved by an organic electroluminescent compound represented by the following formula 1:

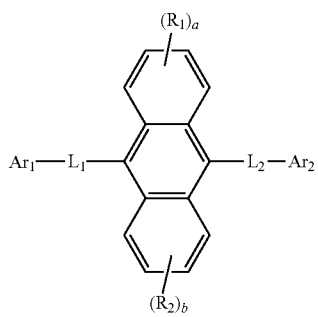

(1)

wherein $L_1$ and $L_2$ each independently represent a single bond, a substituted or unsubstituted (C6-C30)arylene, or a substituted or unsubstituted (5- to 30-membered)heteroarylene;

$Ar_1$ represents a substituted or unsubstituted (C6-C30) aryl, or a substituted or unsubstituted (5- to 30-membered)heteroaryl;

$Ar_2$ represents the following formula 1-1 or 1-2;

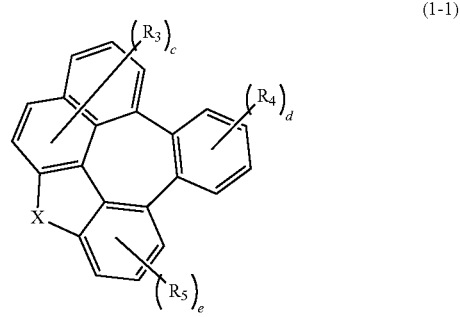

(1-1)

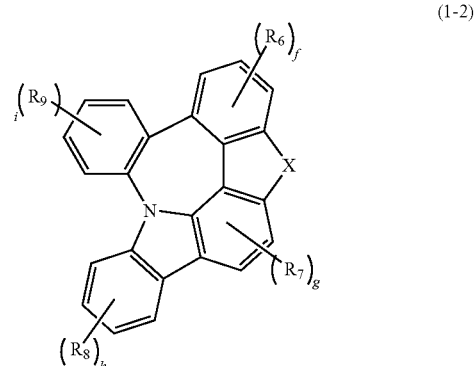

(1-2)

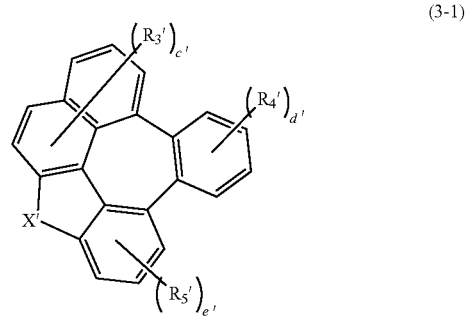

(3-1)

$R_1$ and $R_2$ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

$R_3$ to $R_9$ each independently represent hydrogen, deuterium, a halogen, a cyano, a substituted or unsubstituted (C1-C30)alkyl, a substituted or unsubstituted (C6-C30) aryl, or a substituted or unsubstituted (5- to 30-membered)heteroaryl, or may be linked to $L_2$;

X represents O, S, or N—$R_1$;

$R_{11}$ represents a substituted or unsubstituted (C1-C30) alkyl, a substituted or unsubstituted (C6-C30)aryl, or a substituted or unsubstituted (5- to 30-membered)heteroaryl, or may be linked to $L_2$; and a, b, d, h, and i each independently represent an integer of 1 to 4, c represents an integer of 1 to 5, e and f each independently represent an integer of 1 to 3, and g represents an integer of 1 to 2, where if a to i are an integer of 2 or more, each of $R_1$ to each of $R_9$ may be the same or different.

In addition, the present disclosure provides an organic electroluminescent device comprising a first electrode; a second electrode; and a plurality of organic layers comprising a light-emitting layer between the first electrode and the second electrode, wherein at least two layers of the organic layers comprise one or more of compounds represented by the following formulas 3-1 and 3-2:

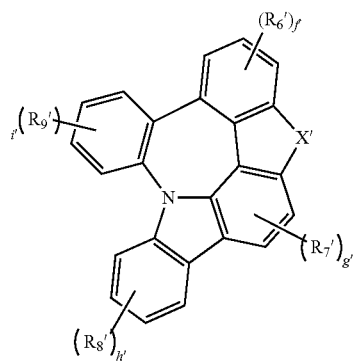

(3-2)

wherein
$R_3'$ to $R_9'$ each independently represent hydrogen, deuterium, a halogen, a cyano, a substituted or unsubstituted (C1-C30)alkyl, a substituted or unsubstituted (C6-C60) aryl, a substituted or unsubstituted (3- to 60-membered) heteroaryl, a substituted or unsubstituted (C3-C30) cycloalkyl, a fused ring group of a substituted or unsubstituted (C3-C30) aliphatic ring(s) and a substituted or unsubstituted (C6-C30) aromatic ring(s), a substituted or unsubstituted (C2-C30)alkenyl, a substituted or unsubstituted (C2-C30)alkynyl, a substituted or unsubstituted (C1-C30)alkoxy, a substituted or unsubstituted (C6-C30)aryloxy, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, substituted or unsubstituted (C1-C30)alkyl(C2-C30)alkenylamino, a substituted or unsubstituted (C1-C30)alkyl(C6-C30) arylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino, or may be linked to an adjacent substituent to form a ring(s);
X' represents O, S, or N—$R_{11}'$;
$R_{11}'$ represents -$L_{11}$-$Ar_3$;
$L_{11}$ represents a single bond, a substituted or unsubstituted (C6-C30)arylene, or a substituted or unsubstituted (5- to 30-membered)heteroarylene;
$Ar_3$ represents hydrogen, a substituted or unsubstituted (C1-C30)alkyl, a substituted or unsubstituted (C6-C30) aryl, a substituted or unsubstituted (5- to 30-membered) heteroaryl, a substituted or unsubstituted mono- or di-(C6-C60)arylamino, a substituted or unsubstituted mono- or di-(3- to 60-membered)heteroarylamino, or a substituted or unsubstituted (C6-C60)aryl(3- to 60-membered)heteroarylamino; and c' represents an integer of 1 to 5, d', h', and i' each independently represent an integer of 1 to 4, e' and f' each independently represent an integer of 1 to 3, and g' represents an integer of 1 to 2, where if c' to i' are an integer of 2 or more, each of $R_3'$ to each of $R_9'$ may be the same or different.

Advantageous Effects of Invention

By using the organic electroluminescent compound of the present disclosure, it is possible to produce an organic electroluminescent device having improved driving voltage, lifetime properties, and/or power efficiency.

MODE FOR THE INVENTION

Hereinafter, the present disclosure will be described in detail. However, the following description is intended to explain the disclosure, and is not meant in any way to restrict the scope of the disclosure.

The term "organic electroluminescent compound" in the present disclosure means a compound that may be used in an organic electroluminescent device. If necessary, the organic electroluminescent compound may be comprised in any layer constituting an organic electroluminescent device.

The term "organic electroluminescent material" in the present disclosure means a material that may be used in an organic electroluminescent device, and may comprise at least one compound. If necessary, the organic electroluminescent material may be comprised in any layer constituting an organic electroluminescent device. For example, the organic electroluminescent material may be a hole injection material, a hole transport material, a hole auxiliary material, a light-emitting auxiliary material, an electron blocking material, a light-emitting material (including a host material and a dopant material), an electron buffer material, a hole blocking material, an electron transport material, an electron transport auxiliary material, an electron injection material, etc.

The organic electroluminescent material of the present disclosure may comprise at least one compound represented by formula 1. The compound represented by formula 1 may be comprised in a hole injection layer, a hole transport layer, a hole auxiliary layer, a light-emitting auxiliary layer, an electron blocking layer, a light-emitting layer (including host and dopant), an electron buffer layer, a hole blocking layer, an electron transport layer, an electron transport auxiliary layer, and an electron injection layer, preferably a light-emitting layer, an electron transport layer, and/or an electron transport auxiliary layer, but is not limited thereto. When comprised in a light-emitting layer, the compound represented by formula 1 may be comprised as a host material or a dopant material, in which the host material may be a host material of a blue, green, or red organic electroluminescent device. Further, when comprised in an electron transport layer, the compound represented by formula 1 may be comprised as an electron transport material. In addition, when comprised in an electron transport auxiliary layer, the compound represented by formula 1 may be comprised as an electron transport auxiliary material.

Herein, the term "(C1-C30)alkyl" is meant to be a linear or branched alkyl having 1 to 30 carbon atoms constituting the chain, in which the number of carbon atoms is preferably 1 to 20, and more preferably 1 to 10. The above alkyl may include methyl, ethyl, n-propyl, iso-propyl, n-butyl, iso-butyl, tert-butyl, etc. The term "(C2-C30)alkenyl" is meant to be a linear or branched alkenyl having 2 to 30 carbon atoms constituting the chain, in which the number of carbon atoms is preferably 2 to 20, and more preferably 2 to 10. The above alkenyl may include vinyl, 1-propenyl, 2-propenyl, 1-butenyl, 2-butenyl, 3-butenyl, 2-methylbut-2-enyl, etc. The term "(C2-C30)alkynyl" is meant to be a linear or branched alkynyl having 2 to 30 carbon atoms constituting the chain, in which the number of carbon atoms is preferably 2 to 20, and more preferably 2 to 10. The above alkynyl may Include ethynyl, 1-propynyl, 2-propynyl, 1-butynyl, 2-butynyl, 3-butynyl, 1-methylpent-2-ynyl, etc. The term "(C3-C30)cycloalkyl" is meant to be a mono- or polycyclic hydrocarbon having 3 to 30 ring backbone carbon atoms, in which the number of carbon atoms is preferably 3 to 20, and more preferably 3 to 7. The above cycloalkyl may include cyclopropyl, cyclobutyl, cyclopentyl, cyclohexyl, etc. The term "(3- to 7-membered)heterocycloalkyl" is meant to be a cycloalkyl having 3 to 7, preferably 5 to 7, ring backbone atoms, and including at least one heteroatom selected from the group consisting of B, N, O, S, Si, and P, and preferably the group consisting of O, S, and N. The above heterocycloalkyl may include tetrahydrofuran, pyrrolidine, thiolan, tetrahydropyran, etc. The term "(C6-C30)aryl(ene)" is meant to be a monocyclic or fused ring radical derived from an aromatic hydrocarbon having 6 to 30 ring backbone carbon atoms, in which the number of the ring backbone carbon atoms is preferably 6 to 25, and more preferably 6 to 18. The above aryl(ene) may be partially saturated, and may comprise a spiro structure. The above aryl may include phenyl, biphenyl, terphenyl, naphthyl, binaphthyl, phenylnaphthyl, naphthylphenyl, phenylterphenyl, fluorenyl, phenylfluorenyl, benzofluorenyl, dibenzofluorenyl, phenanthrenyl, phenylphenanthrenyl, anthracenyl, indenyl, triphenylenyl, pyrenyl, tetracenyl, perylenyl, chrysenyl, naphthacenyl, fluoranthenyl, spirobifluorenyl, azulenyl, etc. More specifically, the above aryl may include phenyl, 1-naphthyl, 2-naphthyl, 1-anthryl, 2-anthryl, 9-anthryl, benzanthryl, 1-phenanthryl, 2-phenanthryl, 3-phenanthryl, 4-phenanthryl, 9-phenanthryl, naphthacenyl, pyrenyl, 1-chrysenyl, 2-chrysenyl, 3-chrysenyl, 4-chrysenyl, 5-chrysenyl, 6-chrysenyl, benzo[c]phenanthryl, benzo[g]chrysenyl, 1-triphenylenyl, 2-triphenylenyl, 3-triphenylenyl, 4-triphenylenyl, 1-fluorenyl, 2-fluorenyl, 3-fluorenyl, 4-fluorenyl, 9-fluorenyl, benzo[a]fluorenyl, benzo[b]fluorenyl, benzo[c]fluorenyl, dibenzofluorenyl, 2-biphenylyl, 3-biphenylyl, 4-biphenylyl, o-terphenyl, m-terphenyl-4-yl, m-terphenyl-3-yl, m-terphenyl-2-yl, p-terphenyl-4-yl, p-terphenyl-3-yl, p-terphenyl-2-yl, m-quaterphenyl, 3-fluoranthenyl, 4-fluoranthenyl, 8-fluoranthenyl, 9-fluoranthenyl, benzofluoranthenyl, o-tolyl, m-tolyl, p-tolyl, 2,3-xylyl, 3,4-xylyl, 2,5-xylyl, mesityl, o-cumenyl, m-cumenyl, p-cumenyl, p-t-butylphenyl, p-(2-phenylpropyl)phenyl, 4'-methylbiphenylyl, 4"-t-butyl-p-terphenyl-4-yl, 9,9-dimethyl-1-fluorenyl, 9,9-dimethyl-2-fluorenyl, 9,9-dimethyl-3-fluorenyl, 9,9-dimethyl-4-fluorenyl, 9,9-diphenyl-1-fluorenyl, 9,9-diphenyl-2-fluorenyl, 9,9-diphenyl-3-fluorenyl, 9,9-diphenyl-4-fluorenyl, 11,11-dimethyl-1-benzo[a]fluorenyl, 11,11-dimethyl-2-benzo[a]fluorenyl, 11,11-dimethyl-3-benzo[a]fluorenyl, 11,11-dimethyl-4-benzo[a]fluorenyl, 11,11-dimethyl-5-benzo[a]fluorenyl, 11,11-dimethyl-6-benzo[a]fluorenyl, 11,11-dimethyl-7-benzo[a]fluorenyl, 11,11-dimethyl-8-benzo[a]fluorenyl, 11,11-dimethyl-9-benzo[a]fluorenyl, 11,11-dimethyl-10-benzo[a]fluorenyl, 11,11-dimethyl-1-benzo[b]fluorenyl, 11,11-dimethyl-2-benzo[b]fluorenyl, 11,11-dimethyl-3-benzo[b]fluorenyl, 11,11-dimethyl-4-benzo[b]fluorenyl, 11,11-dimethyl-5-benzo[b]fluorenyl, 11,11-dimethyl-6-benzo[b]fluorenyl, 11,11-dimethyl-7-benzo[b]fluorenyl, 11,11-dimethyl-8-benzo[b]fluorenyl, 11,11-dimethyl-9-benzo[b]fluorenyl, 11,11-dimethyl-10-benzo[b]fluorenyl, 11,11-dimethyl-1-benzo[c]fluorenyl, 11,11-dimethyl-2-benzo[c]fluorenyl, 11,11-dimethyl-3-benzo[c]fluorenyl, 11,11-dimethyl-4-benzo[c]fluorenyl, 11,11-dimethyl-5-benzo[c]fluorenyl, 11,11-dimethyl-6-benzo[c]fluorenyl, 11,11-dimethyl-7-benzo[c]fluorenyl, 11,11-dimethyl-8-benzo[c]fluorenyl, 11,11-dimethyl-9-benzo[c]fluorenyl, 11,11-dimethyl-10-benzo[c]fluorenyl, 11,11-diphenyl-1-benzo[a]fluorenyl, 11,11-diphenyl-2-benzo[a]fluorenyl, 11,11-diphenyl-3-benzo[a]fluorenyl, 11,11-diphenyl-4-benzo[a]fluorenyl, 11,11-diphenyl-5-benzo[a]fluorenyl, 11,11-diphenyl-6-benzo[a]fluorenyl, 11,11-diphenyl-7-benzo[a]fluorenyl, 11,11-diphenyl-8-benzo[a]fluorenyl, 11,11-diphenyl-9-benzo[a]fluorenyl, 11,11-diphenyl-10-benzo[a]fluorenyl, 11,11-diphenyl-1-benzo[b]fluorenyl, 11,11-diphenyl-2-benzo[b]fluorenyl, 11,11-diphenyl-3-benzo[b]fluorenyl, 11,11-diphenyl-4-benzo[b]fluorenyl, 11,11-diphenyl-5-benzo[b]fluorenyl, 11,11-diphenyl-6-benzo[b]fluorenyl, 11,11-diphenyl-7-benzo[b]fluorenyl, 11,11-diphenyl-8-benzo[b]fluorenyl, 11,11-diphenyl-9-benzo[b]fluorenyl, 11,11-diphenyl-10-benzo[b]fluorenyl, 11,11-diphenyl-1-benzo[c]fluorenyl, 11,11-diphenyl-2-benzo[c]fluorenyl, 11,11-diphenyl-3-benzo[c]fluorenyl, 11,11-diphenyl-4-benzo[c]fluorenyl, 11,11-diphenyl-5-benzo[c]fluorenyl, 11,11-diphenyl-6-benzo[c]fluorenyl, 11,11-diphenyl-7-benzo[c]fluorenyl, 11,11-diphenyl-8-benzo[c]fluorenyl, 11,11-diphenyl-9-benzo[c]fluorenyl, 11,11-diphenyl-10-benzo[c]fluorenyl, etc.

The term "(3- to 30-membered)heteroaryl or (3- to 60-membered)heteroaryl" is meant to be an aryl having 3 to 30 or 3 to 60 ring backbone atoms, and including at least one, preferably 1 to 4 heteroatoms selected from the group consisting of B, N, O, S, Si, and P. The above heteroaryl may be a monocyclic ring, or a fused ring condensed with at least one benzene ring; may be partially saturated; may be one formed by linking at least one heteroaryl or aryl group to a heteroaryl group via a single bond(s); and may comprise a spiro structure. The above heteroaryl may include a monocyclic ring-type heteroaryl such as furyl, thiophenyl, pyrrolyl, imidazolyl, pyrazolyl, thiazolyl, thiadiazolyl, isothiazolyl, isoxazolyl, oxazolyl, oxadiazolyl, triazinyl, tetrazinyl, triazolyl, tetrazolyl, furazanyl, pyridyl, pyrazinyl, pyrimidinyl, and pyridazinyl, and a fused ring-type heteroaryl such as benzofuranyl, benzothiophenyl, isobenzofuranyl, dibenzofuranyl, dibenzothiophenyl, naphthobenzofuranyl, naphthobenzothiophenyl, benzimidazolyl, benzothiazolyl, benzoisothiazolyl, benzoisoxazolyl, benzoxazolyl, isoindolyl, indolyl, benzoindolyl, indazolyl, benzothiadiazolyl, quinolyl, isoquinolyl, cinnolinyl, quinazolinyl, benzoquinazolinyl, quinoxalinyl, benzoquinoxalinyl, naphthyridinyl, carbazolyl, benzocarbazolyl, dibenzocarbazolyl, phenoxazinyl, phenothiazinyl, phenanthridinyl, benzodioxolyl, and dihydroacridinyl. More specifically, the above heteroaryl may include 1-pyrrolyl, 2-pyrrolyl, 3-pyrrolyl, pyrazinyl, 2-pyridinyl, 2-pyrimidinyl, 4-pyrimidinyl, 5-pyrimidinyl, 6-pyrimidinyl, 1,2,3-triazin-4-yl, 1,2,4-triazin-3-yl, 1,3,5-triazin-2-yl, 1-imidazolyl, 2-imidazolyl, 1-pyrazolyl, 1-indolidinyl, 2-indolidinyl, 3-indolidinyl, 5-indolidinyl, 6-indolidinyl, 7-indolidinyl, 8-indolidinyl, 2-imidazopyridinyl, 3-Imidazopyridinyl, 5-imidazopyridinyl, 6-imidazopyridinyl, 7-imidazopyridinyl, 8-imidazopyridinyl, 3-pyridinyl, 4-pyridinyl, 1-indolyl, 2-indolyl, 3-indolyl, 4-indolyl, 5-indolyl, 6-indolyl, 7-indolyl, 1-isoindolyl, 2-isoindolyl, 3-isoindolyl, 4-isoindolyl, 5-isoindolyl, 6-isoindolyl, 7-isoindolyl, 2-furyl, 3-furyl, 2-benzofuranyl, 3-benzofuranyl, 4-benzofuranyl, 5-benzofuranyl, 6-benzofuranyl, 7-benzofuranyl, 1-isobenzofuranyl, 3-isobenzofuranyl, 4-isobenzofuranyl, 5-isobenzofuranyl, 6-isobenzofuranyl, 7-isobenzofuranyl, 2-quinolyl, 3-quinolyl, 4-quinolyl, 5-quinolyl, 6-quinolyl, 7-quinolyl, 8-quinolyl, 1-isoquinolyl, 3-isoquinolyl, 4-isoquinolyl, 5-isoquinolyl, 6-isoquinolyl, 7-isoquinolyl, 8-isoquinolyl, 2-quinoxalinyl, 5-quinoxalinyl, 6-quinoxalinyl, 1-carbazolyl, 2-carbazolyl, 3-carbazolyl, 4-carbazolyl, 9-carbazolyl, azacarbazolyl-1-yl, azacarbazolyl-2-yl, azacarbazolyl-3-yl, azacarbazolyl-4-yl, azacarbazolyl-5-yl, azacarbazolyl-6-yl, azacarbazolyl-7-yl, azacarbazolyl-8-yl, azacarbazolyl-9-yl, 1-phenanthridinyl, 2-phenanthridinyl, 3-phenanthridinyl, 4-phenanthridinyl, 6-phenanthridinyl, 7-phenanthridinyl, 8-phenanthridinyl, 9-phenanthridinyl, 10-phenanthridinyl, 1-acridinyl, 2-acridinyl, 3-acridinyl, 4-acridinyl, 9-acridinyl, 2-oxazolyl, 4-oxazolyl, 5-oxazolyl, 2-oxadiazolyl, 5-oxadiazolyl, 3-furazanyl, 2-thienyl, 3-thienyl, 2-methylpyrrol-1-yl, 2-methylpyrrol-3-yl, 2-methylpyrrol-4-yl, 2-methylpyrrol-5-yl, 3-methylpyrrol-1-yl, 3-methylpyrrol-2-yl, 3-methylpyrrol-4-yl, 3-methylpyrrol-5-yl, 2-t-butylpyrrol-4-yl, 3-(2-phenylpropyl) pyrrol-1-yl, 2-methyl-1-indolyl, 4-methyl-1-indolyl, 2-methyl-3-indolyl, 4-methyl-3-indolyl, 2-t-butyl-1-indolyl, 4-t-butyl-1-indolyl, 2-t-butyl-3-indolyl, 4-t-butyl-3-indolyl, 1-dibenzofuranyl, 2-dibenzofuranyl, 3-dibenzofuranyl, 4-dibenzofuranyl, 1-dibenzothiophenyl, 2-dibenzothiophenyl, 3-dibenzothiophenyl, 4-dibenzothiophenyl, 1-naphtho-[1,2-b]-benzofuranyl, 2-naphtho-[1,2-b]-benzofuranyl, 3-naphtho-[1,2-b]-benzofuranyl, 4-naphtho-[1,2-b]-benzofuranyl, 5-naphtho-[1,2-b]-benzofuranyl, 6-naphtho-[1,2-b]-benzofuranyl, 7-naphtho-[1,2-b]-benzofuranyl, 8-naphtho-[1,2-b]-benzofuranyl, 9-naphtho-[1,2-b]-benzofuranyl, 10-naphtho-[1,2-b]-benzofuranyl, 1-naphtho-[2,3-b]-benzofuranyl, 2-naphtho-[2,3-b]-benzofuranyl, 3-naphtho-[2,3-b]-benzofuranyl, 4-naphtho-[2,3-b]-benzofuranyl, 5-naphtho-[2,3-b]-benzofuranyl, 6-naphtho-[2,3-b]-benzofuranyl, 7-naphtho-[2,3-b]-benzofuranyl, 8-naphtho-[2,3-b]-benzofuranyl, 9-naphtho-[2,3-b]-benzofuranyl, 10-naphtho-[2,3-b]-benzofuranyl, 1-naphtho-[2,1-b]-benzofuranyl, 2-naphtho-[2,1-b]-benzofuranyl, 3-naphtho-[2,1-b]-benzofuranyl, 4-naphtho-[2,1-b]-benzofuranyl, 5-naphtho-[2,1-b]-benzofuranyl, 6-naphtho-[2,1-b]-benzofuranyl, 7-naphtho-[2,1-b]-benzofuranyl, 8-naphtho-[2,1-b]-benzofuranyl, 9-naphtho-[2,1-b]-benzofuranyl, 10-naphtho-[2,1-b]-benzofuranyl, 1-naphtho-[1,2-b]-benzothiophenyl, 2-naphtho-[1,2-b]-benzothiophenyl, 3-naphtho-[1,2-b]-benzothiophenyl, 4-naphtho-[1,2-b]-benzothiophenyl, 5-naphtho-[1,2-b]-benzothiophenyl, 6-naphtho-[1,2-b]-benzothiophenyl, 7-naphtho-[1,2-b]-benzothiophenyl, 8-naphtho-[1,2-b]-benzothiophenyl, 9-naphtho-[1,2-b]-benzothiophenyl, 10-naphtho-[1,2-b]-benzothiophenyl, 1-naphtho-[2,3-b]-benzothiophenyl, 2-naphtho-[2,3-b]-benzothiophenyl, 3-naphtho-[2,3-b]-benzothiophenyl, 4-naphtho-[2,3-b]-benzothiophenyl, 5-naphtho-[2,3-b]-benzothiophenyl, 1-naphtho-[2,1-b]-benzothiophenyl, 2-naphtho-[2,1-b]-benzothiophenyl, 3-naphtho-[2,1-b]-benzothiophenyl, 4-naphtho-[2,1-b]-benzothiophenyl, 5-naphtho-[2,1-b]-benzothiophenyl, 6-naphtho-[2,1-b]-benzothiophenyl, 7-naphtho-[2,1-b]-benzothiophenyl, 8-naphtho-[2,1-b]-benzothiophenyl, 9-naphtho-[2,1-b]-benzothiophenyl, 10-naphtho-[2,1-b]-benzothiophenyl, 1-silafluorenyl, 2-silafluorenyl, 3-silafluorenyl, 4-silafluorenyl, 1-germafluorenyl, 2-germafluorenyl, 3-germafluorenyl, 4-germafluorenyl, etc. Furthermore, "halogen" includes F, Cl, Br, and I.

In addition, "ortho (o-)." "meta (m-)," and "para (p-)" are prefixes, which represent the relative positions of substituents respectively. Ortho indicates that two substituents are adjacent to each other, and for example, when two substituents in a benzene derivative occupy positions 1 and 2, it is called an ortho position. Meta indicates that two substituents are at positions 1 and 3, and for example, when two substituents in a benzene derivative occupy positions 1 and 3, it is called a meta position. Para indicates that two substituents are at positions 1 and 4, and for example, when two substituents in a benzene derivative occupy positions 1 and 4, it is called a para position.

Herein, "substituted" in the expression "substituted or unsubstituted" means that a hydrogen atom in a certain functional group is replaced with another atom or another functional group, i.e., a substituent. The substituents of the substituted alkyl, the substituted aryl, the substituted arylene, the substituted heteroaryl, the substituted heteroarylene, the substituted cycloalkyl, the substituted aliphatic ring, the substituted aromatic ring, the substituted alkenyl, the substituted alkynyl, the substituted alkoxy, the substituted aryloxy, the substituted mono- or di-alkylamino, the substituted mono- or di-alkenylamino, the substituted mono- or di-arylamino, the substituted mono- or di-heteroarylamino, the substituted alkylalkenylamino, the substituted alkylarylamino, the substituted alkylheteroarylamino, the substituted alkenylarylamino, the substituted alkenylheteroarylamino, and the substituted arylheteroarylamino in the formulas of the present disclosure each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30) alkyl(s) and a (3- to 30-membered)heteroaryl(s); a tri(C1-C30)alkylsilyl; a tri(C6-C30)arylsilyl; a di(C1-C30)alkyl (C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl (C6-C30)arylamino; a (C1-C30)alkyl(3- to 30-membered) heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30) arylcarbonyl; a di(C6-C30)arylboronyl; a di(C1-C30)alkylboronyl; a (C1-C30)alkyl(C6-C30)arylboronyl; a (C6-C30) aryl(C1-C30)alkyl; and a (C1-C30)alkyl(C6-C30)aryl, and the substituents may be substituted with deuterium instead of hydrogen in an optional position. According to one embodiment of the present disclosure, the substituents each independently are at least one selected from the group consisting of a (C1-C6)alkyl, and a (C6-C25)aryl. Specifically, the substituents each independently may be at least one selected from the group consisting of a methyl and a naphthyl.

In the formulas of the present disclosure, if a substituent is linked to an adjacent substituent to form a ring, the ring may be a substituted or unsubstituted, mono- or polycyclic, (3- to 30-membered) aliphatic or aromatic ring, or the combination thereof, which two or more adjacent substituents are linked to form. In addition, the formed ring may contain at least one heteroatom selected from B, N, O, S, Si, and P, preferably at least one heteroatom selected from N, O, and S. According to one embodiment of the present disclosure, the number of the ring backbone atoms is 5 to 20.

According to another embodiment of the present disclosure, the number of the ring backbone atoms is 5 to 15.

In the formulas of the present disclosure, heteroaryl(ene) may each independently contain at least one heteroatom selected from B, N, O, S, Si, and P. In addition, the heteroatom may be bonded to at least one selected from the group consisting of hydrogen, deuterium, a halogen, a cyano, a substituted or unsubstituted (C1-C30)alkyl, a substituted or unsubstituted (C6-C30)aryl, a substituted or unsubstituted (5- to 30-membered)heteroaryl, a substituted or unsubstituted (C3-C30)cycloalkyl, a substituted or unsubstituted (C1-C30)alkoxy, a substituted or unsubstituted tri(C1-C30)alkylsilyl, a substituted or unsubstituted di(C1-C30)alkyl(C6-C30)arylsilyl, a substituted or unsubstituted (C1-C30)alkyldi(C6-C30)arylsilyl, a substituted or unsubstituted tri(C6-C30)arylsilyl, a substituted or unsubstituted mono- or di-(C1-C30)alkylamino, a substituted or unsubstituted mono- or di-(C6-C30)arylamino, and a substituted or unsubstituted (C1-C30)alkyl(C6-C30)arylamino.

Hereinafter, the compound represented by formula 1 will be described in more detail.

According to one embodiment of the present disclosure, the compound represented by formula 1 may be represented by any one of the following formulas 2-1 to 2-9:

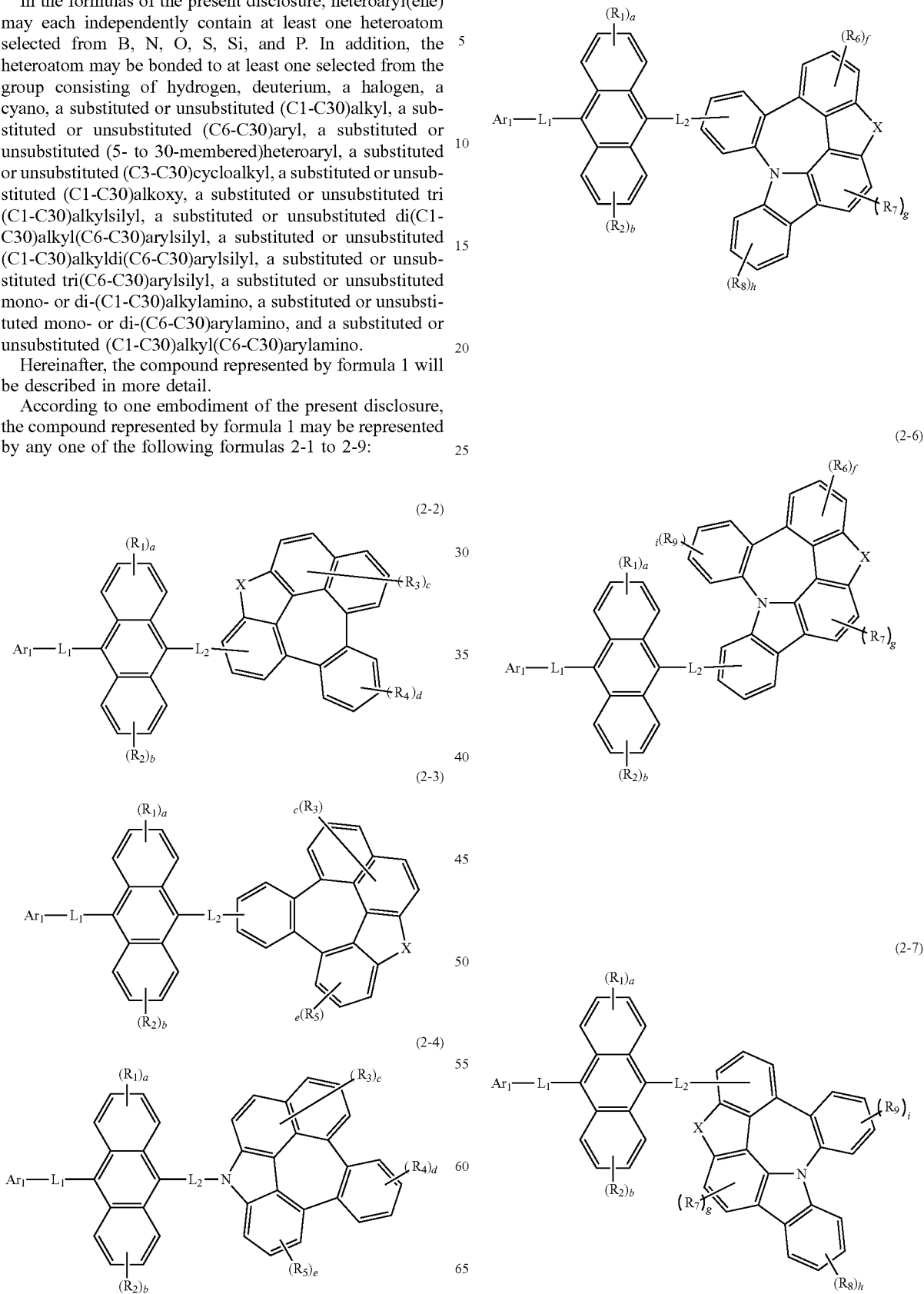

-continued (2-8)

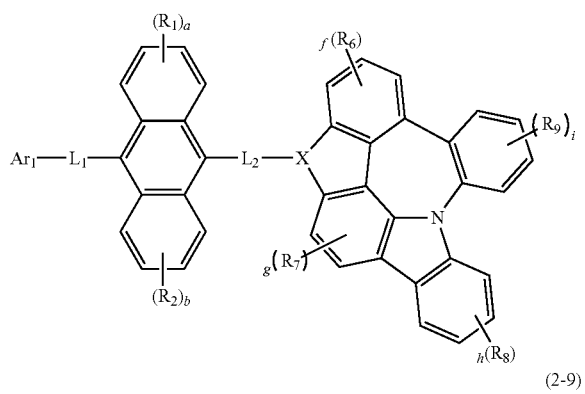

(2-9)

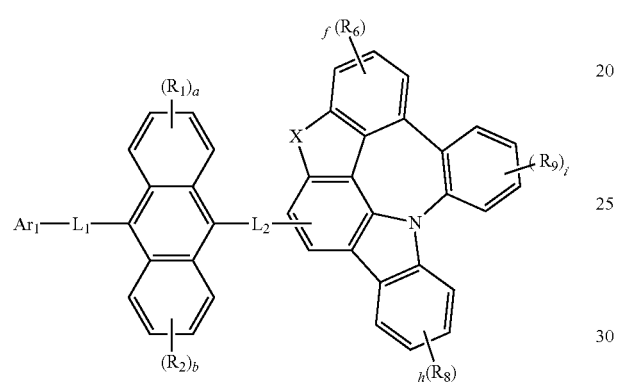

wherein

Ar₁, R₁ to R₉, L₁, L₂, X, and a to i are as defined in formula 1.

In formula 1, L₁ and L₂ each independently represent a single bond, a substituted or unsubstituted (C6-C30)arylene, or a substituted or unsubstituted (5- to 30-membered)heteroarylene. According to one embodiment of the present disclosure, L₁ and L₂ each independently represent a single bond, or a substituted or unsubstituted (C6-C15)arylene. According to another embodiment of the present disclosure, L₁ and L₂ each independently represent a single bond or an unsubstituted (C6-C15)arylene. Specifically, L₁ and L₂ may each independently represent a single bond, phenylene, etc.

In formula 1, Ar₁ represents a substituted or unsubstituted (C6-C30)aryl, or a substituted or unsubstituted (5- to 30-membered)heteroaryl. According to one embodiment of the present disclosure, Ar₁ represents a substituted or unsubstituted (C6-C12)aryl. According to another embodiment of the present disclosure, Ar₁ represents an unsubstituted (C6-C12)aryl. Specifically, Ar₁ may represent a phenyl, naphthyl, etc.

In formula 1, R₁ and R₂ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl. According to one embodiment of the present disclosure, R₁ and R₂ each independently represent hydrogen.

In formulas 1-1 and 1-2, R₃ to R₉ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl, or may be linked to L₂.

According to one embodiment of the present disclosure, R₃ to R₉ each independently represent hydrogen or may be linked to L₂.

In formulas 1-1 and 1-2, X represents O, S, or N—R₁₁.

Herein, R₁₁ represents a substituted or unsubstituted (C1-C30)alkyl, a substituted or unsubstituted (C6-C30)aryl, or a substituted or unsubstituted (5- to 30-membered)heteroaryl, or may be linked to L₂.

In formulas 1, 1-1, and 1-2, a, b, d, h, and i each independently represent an integer of 1 to 4, c represents an integer of 1 to 5, e and f each independently represent an integer of 1 to 3, and g represents an integer of 1 to 2, where if a to i are an integer of 2 or more, each of R₁ to each of R₉ may be the same or different.

The compound represented by formula 1 may be one selected from the following compounds, but is not limited thereto.

1-1

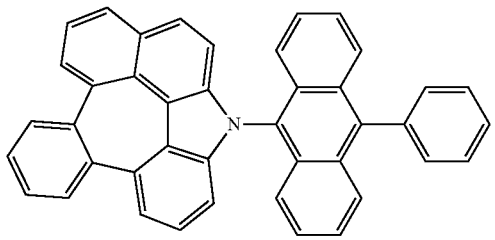

1-2

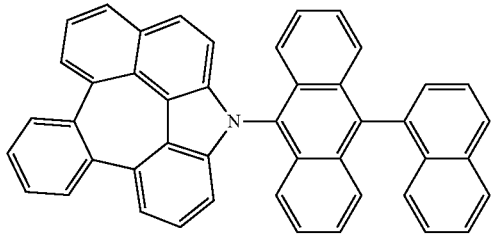

1-3

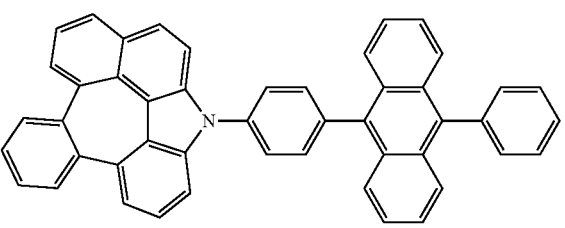

1-4

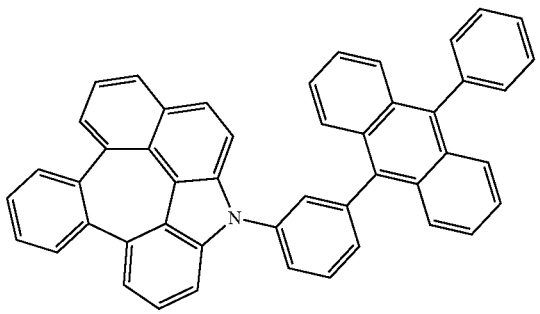

1-5
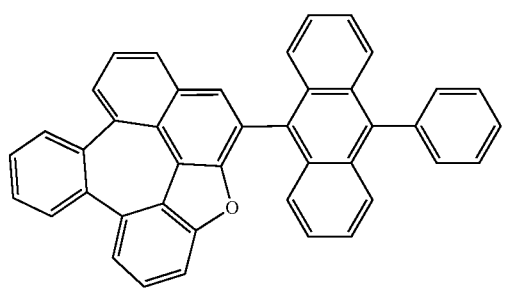
1-6
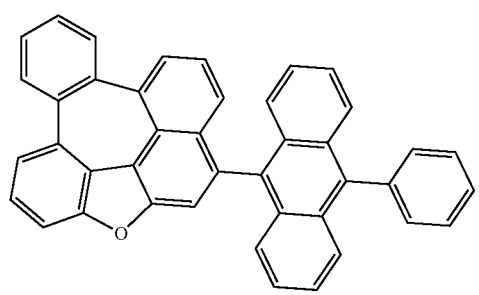
1-7
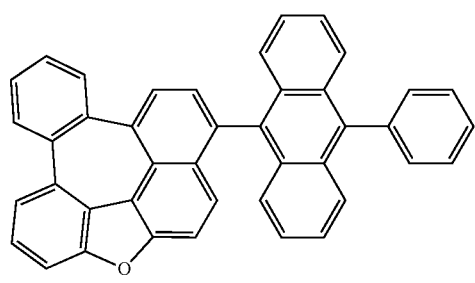
1-8
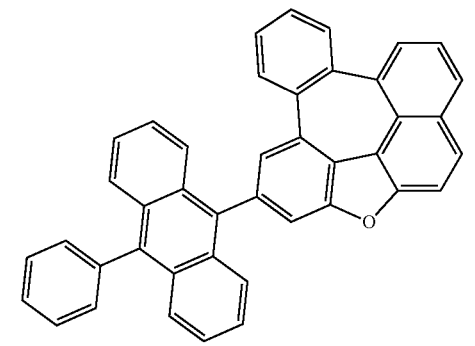
1-9
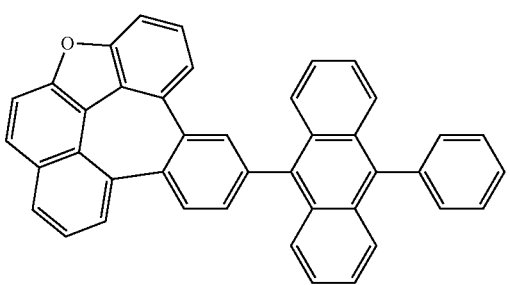
1-10
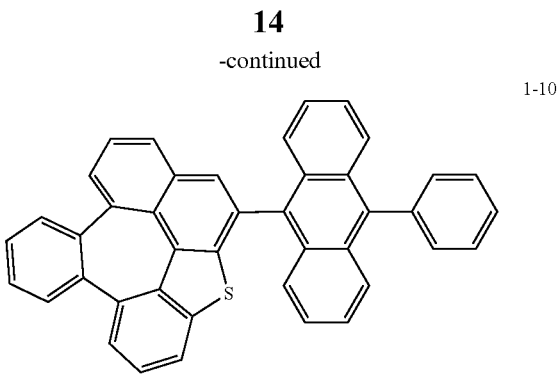
1-11
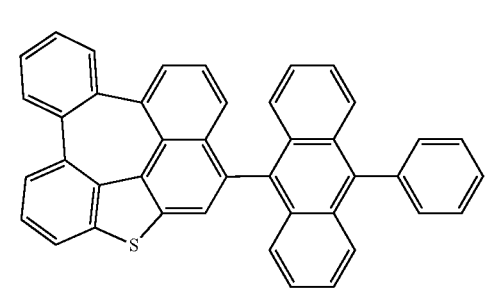
1-12
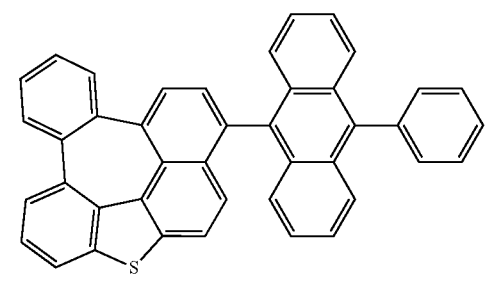
1-13
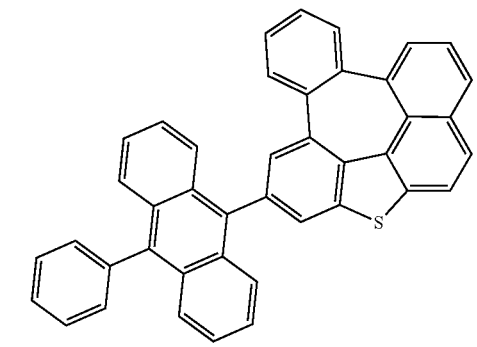
1-14
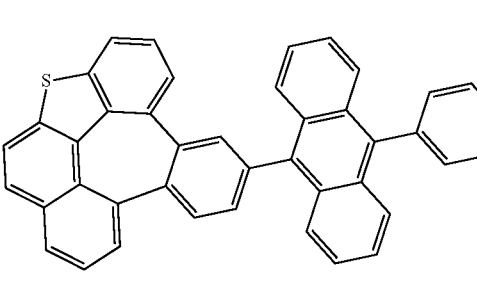

1-15
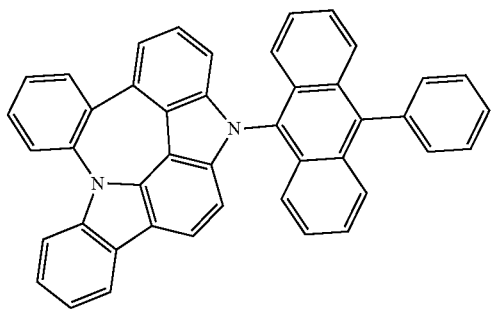
1-16
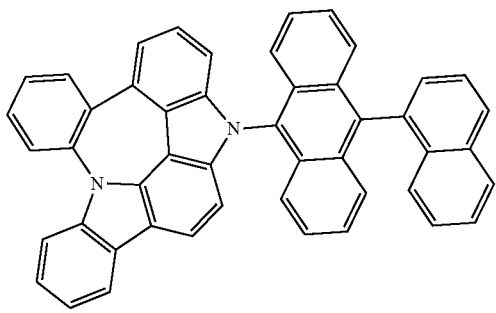
The compound represented by formula 1 of the present disclosure may be produced by a synthetic method known to one skilled in the art, and for example, according to the following reaction schemes 1 to 4, but is not limited thereto:
[Reaction Scheme 1]
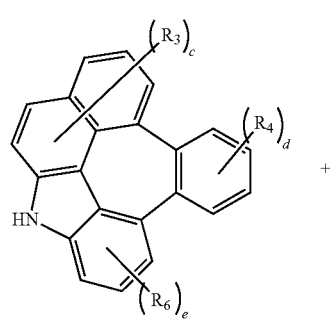
+
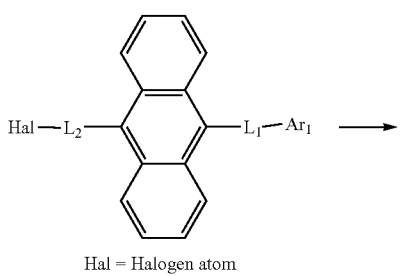
Hal = Halogen atom
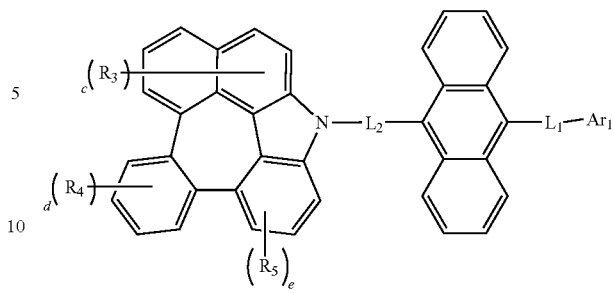
[Reaction Scheme 2]
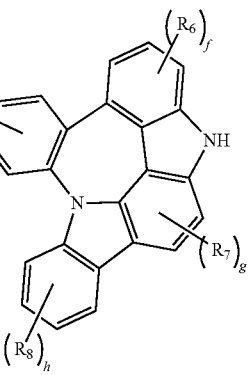
+
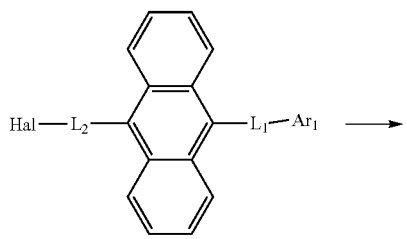
Hal = Halogen atom
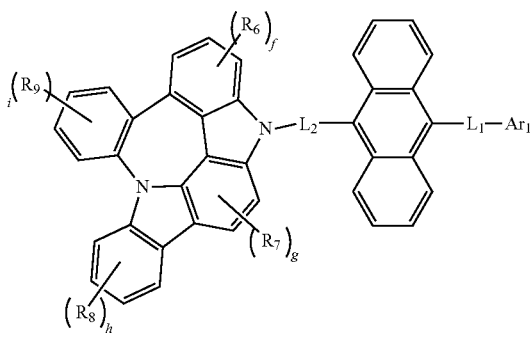
[Reaction Scheme 3]
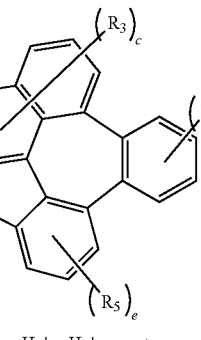
Hal +
Hal = Halogen atom

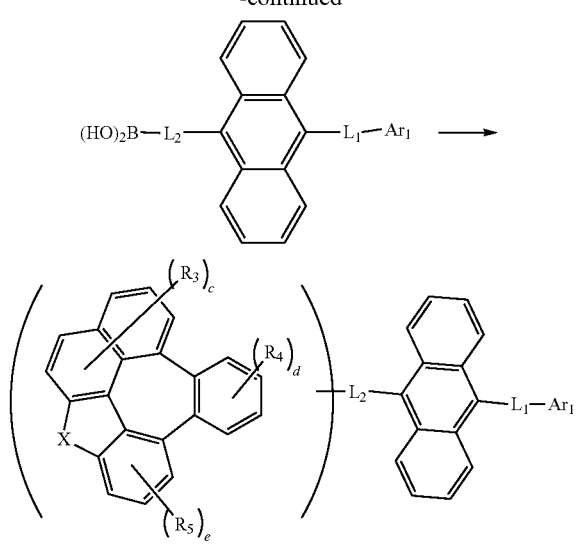

[Reaction Scheme 4]

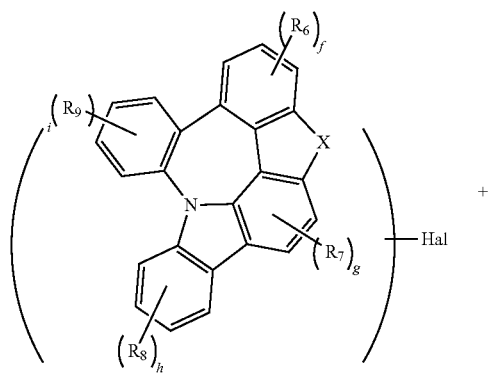

Hal = Halogen atom

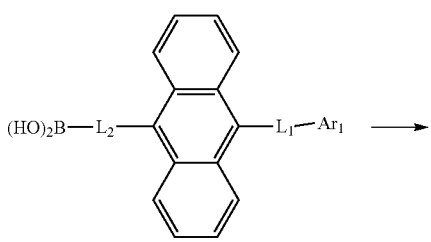

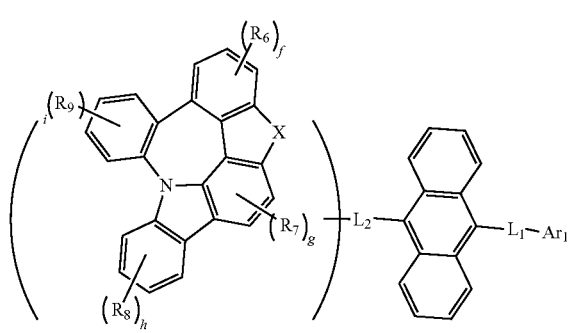

In reaction schemes 1 to 4, $L_1$, $L_2$, $Ar_1$, $R_1$ to $R_9$, X, and a to i are as defined in formula 1, formula 1-1, and formula 1-2.

Although illustrative synthesis examples of the compound represented by formula 1 are described above, one skilled in the art will be able to readily understand that all of them are based on a Buchwald-Hartwig cross-coupling reaction, an N-arylation reaction, an H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an $SN_1$ substitution reaction, an $SN_2$ substitution reaction, a Phosphine-mediated reductive cyclization reaction, etc., and the reactions above proceed even when substituents which are defined in formula 1 above, but are not specified in the specific synthesis examples, are bonded.

The present disclosure provides an organic electroluminescent material comprising the compound represented by formula 1, and an organic electroluminescent device comprising the organic electroluminescent material. The organic electroluminescent material may consist of the compound according to the present disclosure alone, or may further comprise conventional materials included in organic electroluminescent materials.

If necessary, the organic electroluminescent compound of formula 1 of the present disclosure may be used as a co-host material. That is, the light-emitting layer may further include an organic electroluminescent compound other than the organic electroluminescent compound represented by formula 1 of the present disclosure (first host material) as a second host material. In this case, the weight ratio between the first host material and the second host material is in the range of about 1:99 to about 99:1, preferably about 10:90 to about 90:10, and more preferably about 30:70 to about 70:30. Also, the first host material and the second host material may be combined in an amount of a desired ratio by placing them in a shaker and then mixing them; by placing them in a glass tube, dissolving them by heating, and then collecting the resultant; or by dissolving them in a solvent, etc. When two or more materials are included in one layer, mixed deposition may be performed to form a layer, or co-deposition may be performed separately at the same time to form a layer.

The dopant comprised in the organic electroluminescent device of the present disclosure is at least one phosphorescent or fluorescent dopant, and preferably may be a fluorescent dopant. The fluorescent dopant material applied to the organic electroluminescent device of the present disclosure is not particularly limited.

The organic electroluminescent device according to the present disclosure may comprise a first electrode; a second electrode; and a plurality of organic layers comprising a light-emitting layer between the first electrode and the second electrode. The organic layers may comprise a light-emitting layer, a light-emitting auxiliary layer between the light-emitting layer and the first electrode, a hole transport layer between the light-emitting auxiliary layer and the first electrode, an electron transport auxiliary layer between the light-emitting layer and the second electrode, and an electron transport layer between the electron transport auxiliary layer and the second electrode. At least two layers of the organic layers may comprise one or more of compounds represented by the following formulas 3-1 and 3-2:

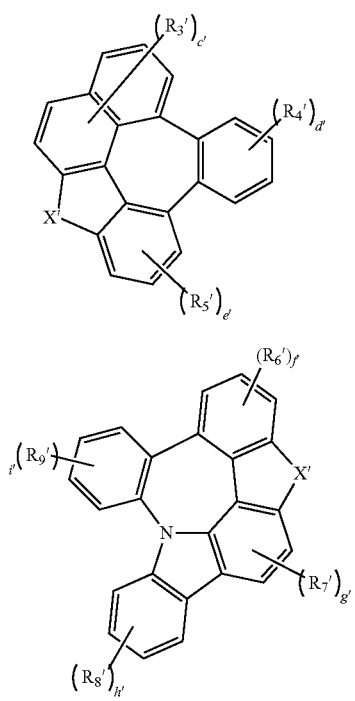

(3-1)

(3-2)

wherein

R$_3$' to R$_9$' each independently represent hydrogen, deuterium, a halogen, a cyano, a substituted or unsubstituted (C1-C30)alkyl, a substituted or unsubstituted (C6-C60) aryl, a substituted or unsubstituted (3- to 60-membered) heteroaryl, a substituted or unsubstituted (C3-C30) cycloalkyl, a fused ring group of a substituted or unsubstituted (C3-C30) aliphatic ring(s) and a substituted or unsubstituted (C6-C30) aromatic ring(s), a substituted or unsubstituted (C2-C30)alkenyl, a substituted or unsubstituted (C2-C30)alkynyl, a substituted or unsubstituted (C1-C30)alkoxy, a substituted or unsubstituted (C6-C30)aryloxy, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30) arylamino, a substituted or unsubstituted (C1-C30) alkyl(3- to 30-membered)heteroarylamino, a substituted or unsubstituted (C2-C30)alkenyl(C6-C30) arylamino, a substituted or unsubstituted (C2-C30) alkenyl(3- to 30-membered)heteroarylamino, or a substituted or unsubstituted (C6-C30)aryl(3- to 30-membered)heteroarylamino, or may be linked to an adjacent substituent to form a ring(s);

X' represents O, S, or N—R$_{11}$;

R$_{11}$' represents -L$_{11}$-Ar$_3$;

L$_{11}$ represents a single bond, a substituted or unsubstituted (C6-C30)arylene, or a substituted or unsubstituted (5- to 30-membered)heteroarylene;

Ar$_3$ represents hydrogen, a substituted or unsubstituted (C1-C30)alkyl, a substituted or unsubstituted (C6-C30) aryl, a substituted or unsubstituted (5- to 30-membered) heteroaryl, a substituted or unsubstituted mono- or di-(C6-C60)arylamino, a substituted or unsubstituted mono- or di-(3- to 60-membered)heteroarylamino, or a substituted or unsubstituted (C6-C60)aryl(3- to 60-membered)heteroarylamino; and c' represents an integer of 1 to 5, d', h', and i' each independently represent an integer of 1 to 4, e' and f each independently represent an integer of 1 to 3, and g' represents an integer of 1 to 2, where if c' to i' are an integer of 2 or more, each of R$_3$' to each of R$_9$' may be the same or different.

According to one embodiment of the present disclosure, the compound represented by formula 3-1 or 3-2 may be comprised in at least the light-emitting layer.

In addition, according to one embodiment of the present disclosure, the compound represented by formula 3-1 or 3-2 may be comprised in at least one layer of the organic layers between the first electrode and the light-emitting layer. For example, the compound may be comprised in one or more of a hole injection layer, a hole transport layer, a hole auxiliary layer, a light-emitting auxiliary layer, an electron blocking layer, a light-emitting layer (including host and dopant), an electron buffer layer, a hole blocking layer, an electron transport layer, an electron transport auxiliary layer, and an electron injection layer, and preferably one or more of a hole transport layer, an electron transport layer, and an electron transport auxiliary layer, but is not limited thereto.

According to one embodiment of the present disclosure, the compound represented by formula 3-1 or 3-2 may be comprised, individually or together, in at least two layers of a hole injection layer, a hole transport layer, a hole auxiliary layer, a light-emitting auxiliary layer, an electron blocking layer, and a light-emitting layer (including host and dopant) of an organic electroluminescent device; or individually or together, in at least two layers of a light-emitting layer (including host and dopant), an electron buffer layer, a hole blocking layer, an electron transport layer, an electron transport auxiliary layer, and an electron injection layer.

The compound represented by formula 3-1 or 3-2 of the present disclosure may be produced by a synthetic method known to one skilled in the art, and for example, according to the methods disclosed in Korean Patent Application Laying-Open Nos. 2018-0099510 (published on Sep. 5, 2018), 2018-0012709 (published on Feb. 6, 2018), etc., but is not limited thereto.

As a specific embodiment, the compound of formula 3-1 or 3-2 comprised in at least one organic layer is represented by formula 1, and the compound of formula 3-1 or 3-2 comprised in at least another organic layer is represented by formula 4.

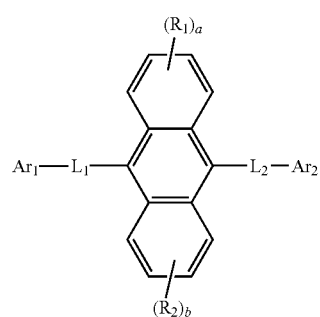

(1)

wherein

L₁ and L₂ each independently represent a single bond, a substituted or unsubstituted (C6-C30)arylene, or a substituted or unsubstituted (5- to 30-membered)heteroarylene;

Ar₁ represents a substituted or unsubstituted (C6-C30) aryl, or a substituted or unsubstituted (5- to 30-membered)heteroaryl;

Ar₂ represents the following formula 1-1 or 1-2;

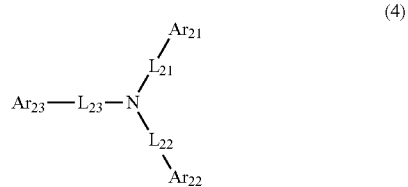
(4)

wherein at least one of Ar₂₁ to Ar₂₃ each independently represent the following formula 1-1 or 1-2, and the other(s) of Ar₂₁ to Ar₂₃ each independently represent a substituted or unsubstituted (C6-C30)aryl, or a substituted or unsubstituted (5- to 30-membered)heteroaryl;

L₂₁ to L₂₃ each independently represent a single bond, a substituted or unsubstituted (C6-C30)arylene, or a substituted or unsubstituted (5- to 30-membered)heteroarylene;

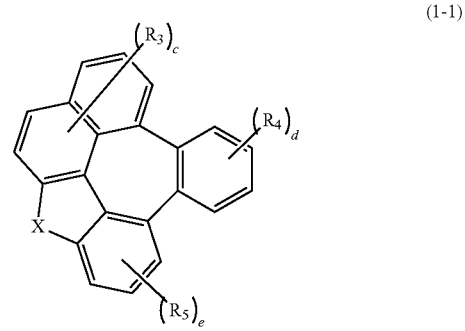
(1-1)

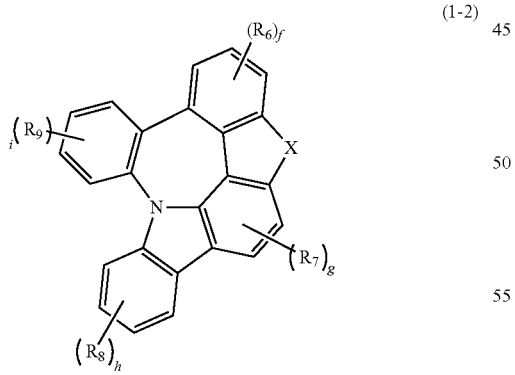
(1-2)

R₁ and R₂ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

R₃ to R₉ each independently represent hydrogen, deuterium, a halogen, a cyano, a substituted or unsubstituted (C1-C30)alkyl, a substituted or unsubstituted (C6-C30) aryl, or a substituted or unsubstituted (5- to 30-membered)heteroaryl, or may be linked to L₂, or also may be linked to one or more of L₂₁ to L₂₃;

X represents O, S, or N—R₁₁;

R₁₁ represents a substituted or unsubstituted (C1-C30) alkyl, a substituted or unsubstituted (C6-C30)aryl, or a substituted or unsubstituted (5- to 30-membered)heteroaryl, or may be linked to L₂, or also may be linked to one or more of L₂₁ to L₂₃; and a, b, d, h, and i each independently represent an integer of 1 to 4, c represents an integer of 1 to 5, e and f each independently represent an integer of 1 to 3, and g represents an integer of 1 to 2, where if a to i are an integer of 2 or more, each of R₁ to each of R₉ may be the same or different.

According to one embodiment of the present disclosure, in formula 4, at least one of Ar₂₁ to Ar₂₃ each independently represent formula 1-1 or 1-2, and the other(s) of Ar₂₁ to Ar₂₃ each independently represent a substituted or unsubstituted (C6-C20)aryl, or a substituted or unsubstituted (5- to 15-membered)heteroaryl. According to another embodiment of the present disclosure, at least one of Ar₂₁ to Ar₂₃ each independently represent formula 1-1 or 1-2, and the other(s) of Ar₂₁ to Ar₂₃ each independently represent a (C6-C20)aryl unsubstituted or substituted with a (C1-C6)alkyl(s) and/or a (C6-C12)aryl(s), or an unsubstituted (5- to 15-membered) heteroaryl. Specifically, Ar₂₁ to Ar₂₃ each independently may represent formula 1-1 or 1-2, and the other(s) of Ar₂₁ to Ar₂₃ each independently may represent a phenyl, naphthyl, biphenyl, naphthylphenyl, dimethylfluorenyl, dibenzofuranyl, etc.

According to one embodiment of the present disclosure, in formula 4, L₂₁ to L₂₃ each independently represent a single bond, or a substituted or unsubstituted (C6-C15) arylene. According to another embodiment of the present disclosure, L₂₁ to L₂₃ each independently represent a single bond, or an unsubstituted (C6-C15)arylene. Specifically, L₂₁ to L₂₃ each independently may represent a single bond, phenylene, biphenylene, etc.

The compound represented by formula 4 may be one selected from the following compounds, but is not limited thereto.

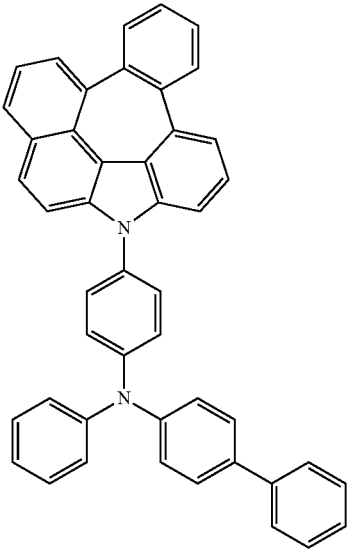
2-1

2-2
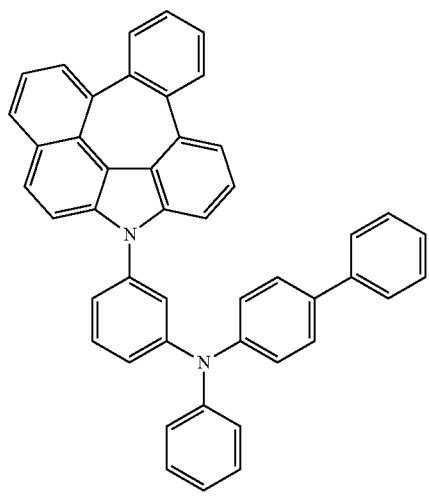
2-3
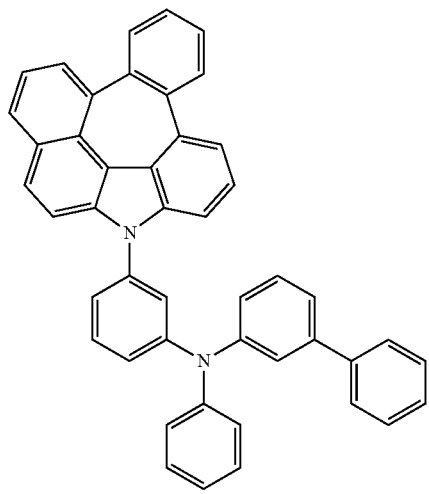
2-4
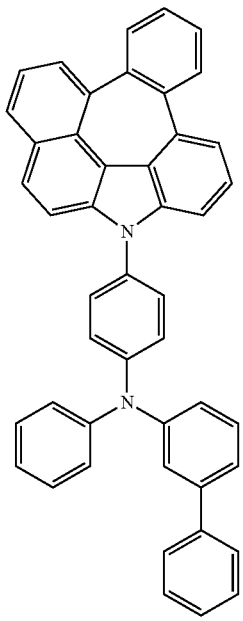
2-5
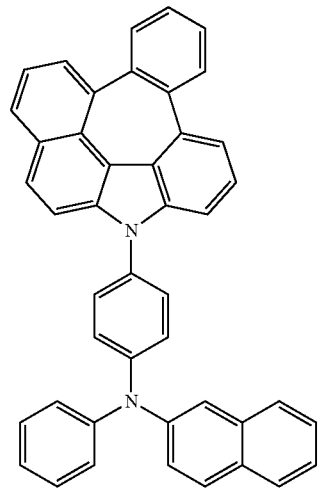
2-6
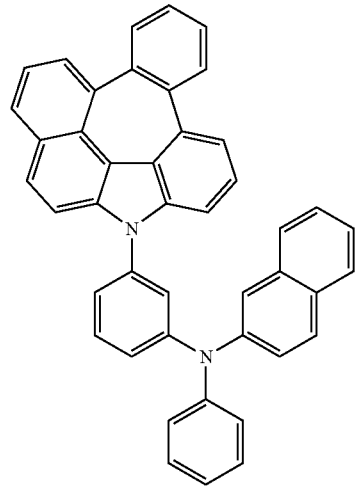
2-7
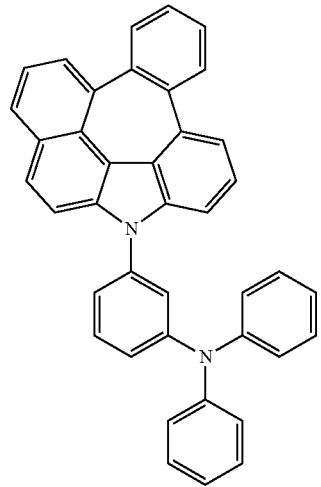

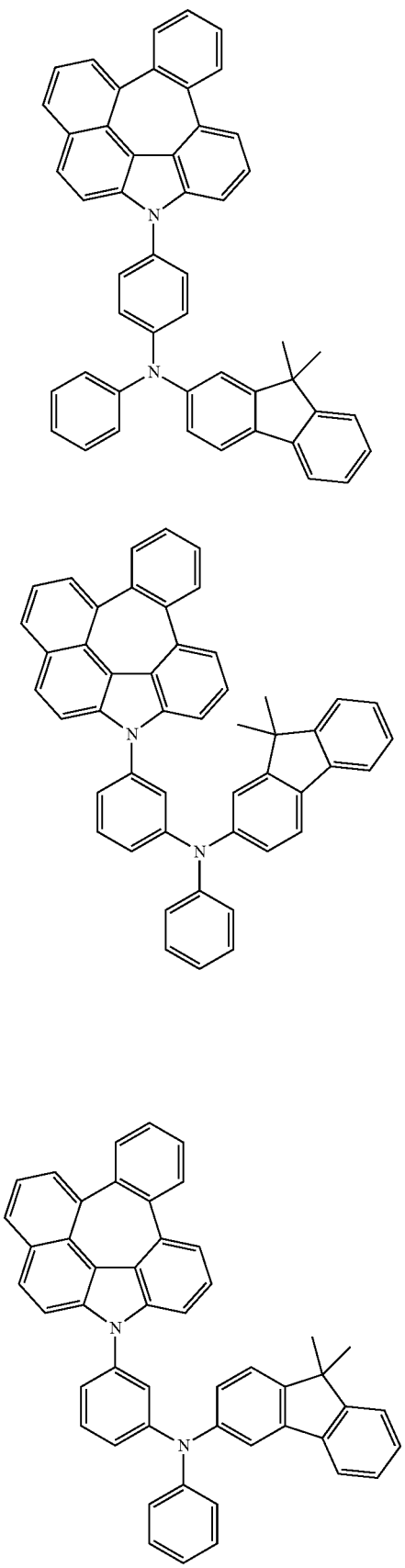
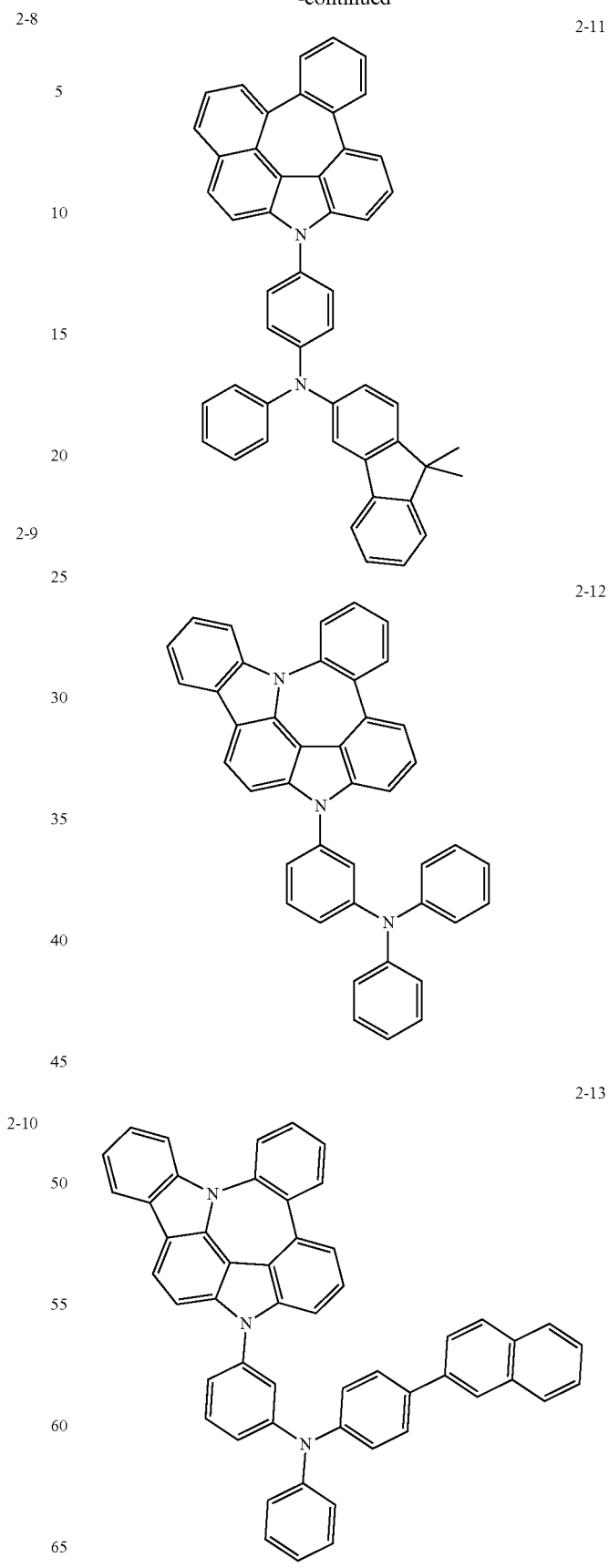

27
-continued
2-14
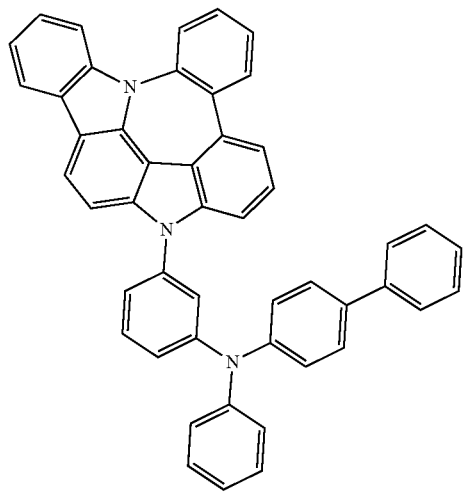
2-15
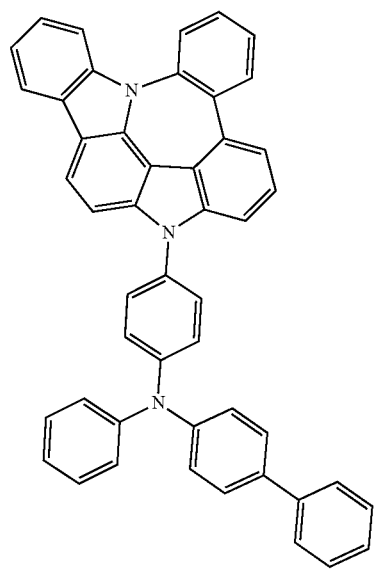
2-16
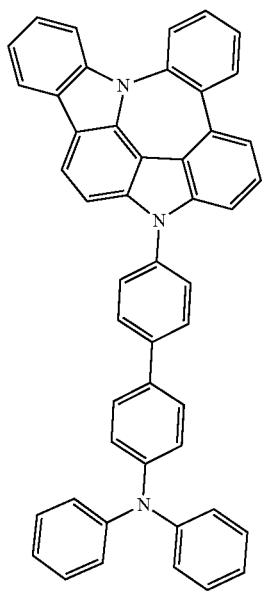
28
-continued
2-17
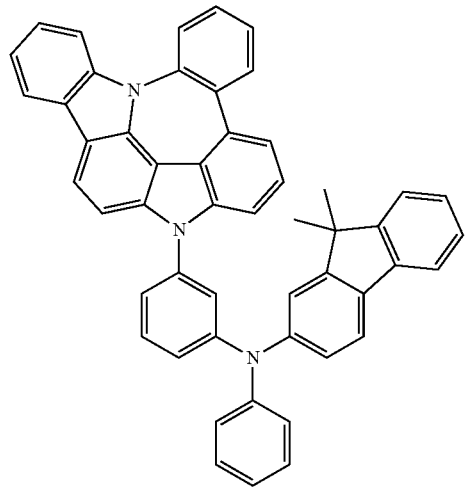
2-18
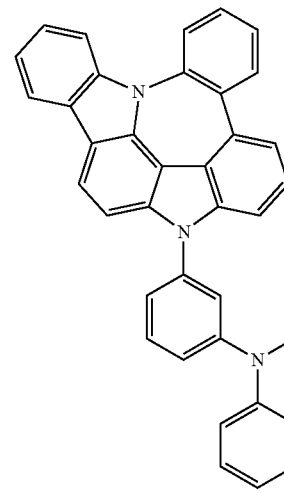
2-19
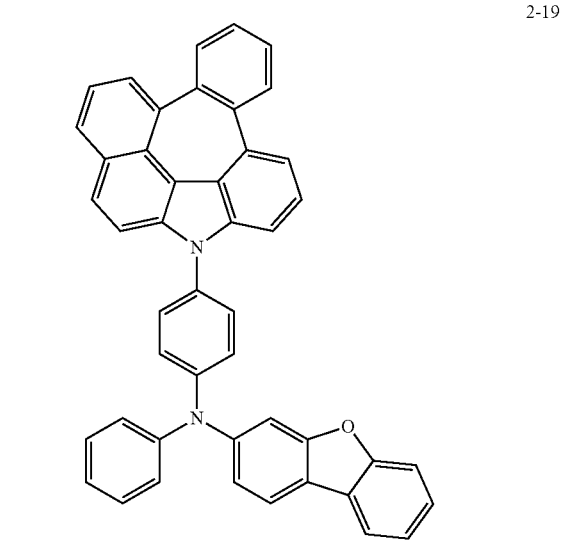

2-20
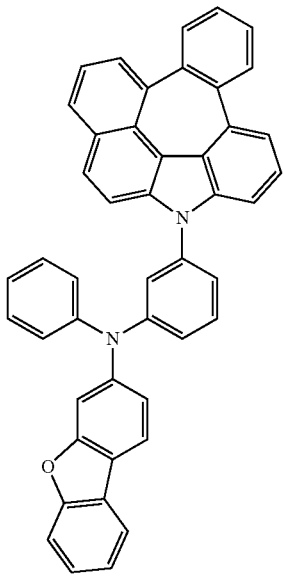
2-22
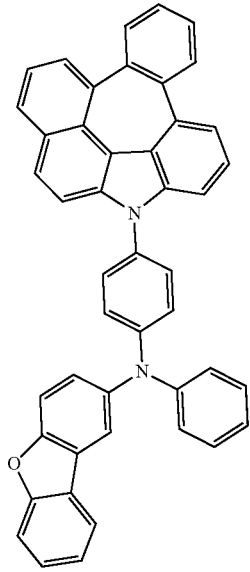
2-21
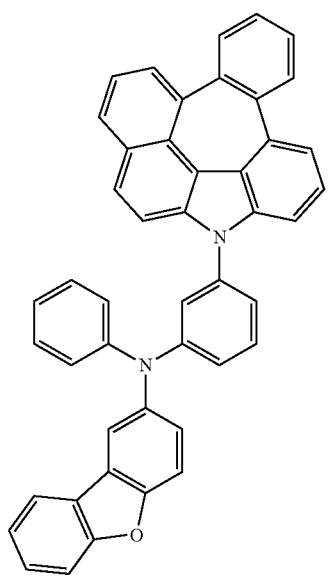
2-23
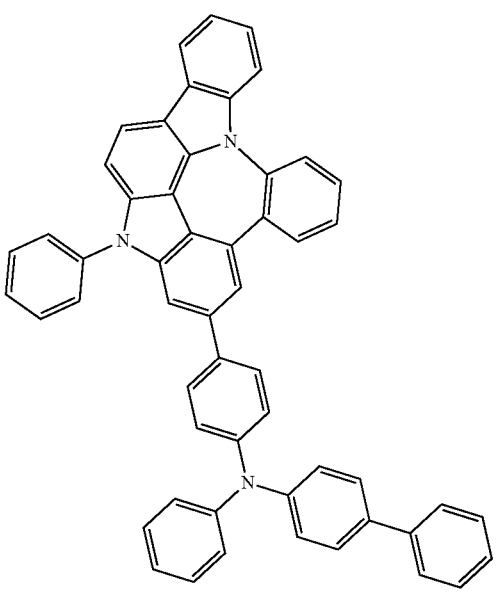

2-24
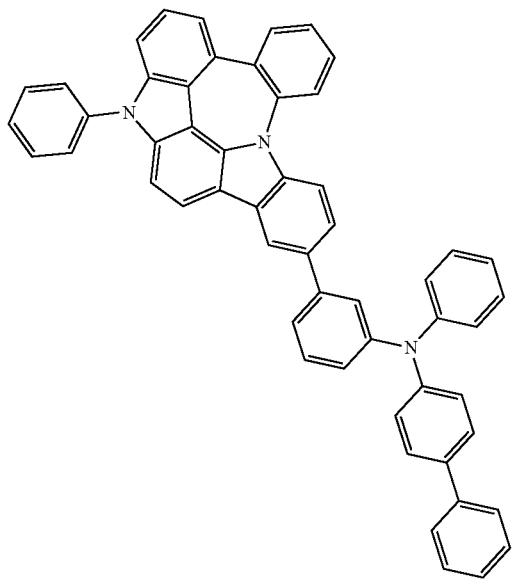
The compound represented by formula 4 of the present disclosure may be produced by a synthetic method known to one skilled in the art, and for example, according to the following reaction schemes 5 to 8, but is not limited thereto:
[Reaction Scheme 5]
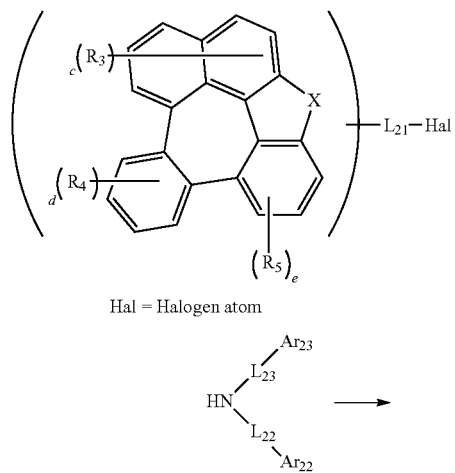
[Reaction Scheme 6]
[Reaction Scheme 7]
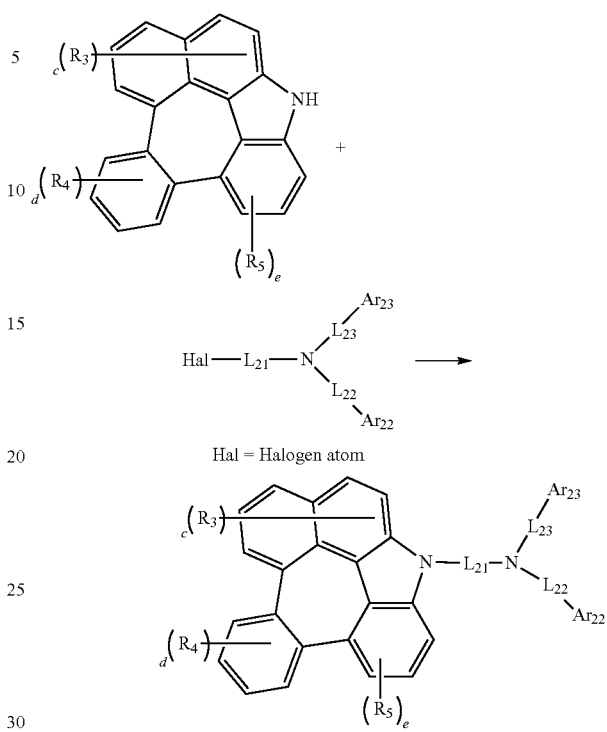
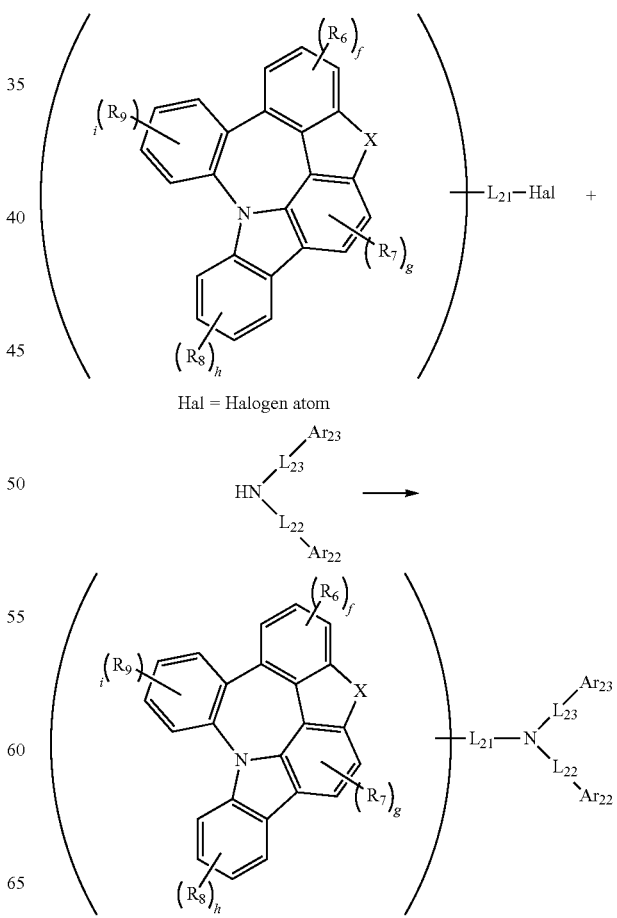

-continued
[Reaction Scheme 8]

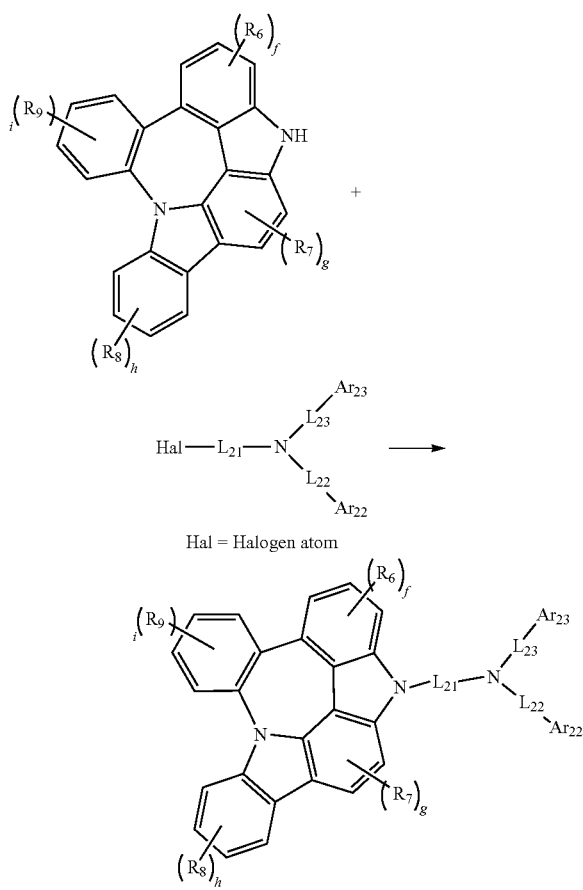

Hal = Halogen atom

In reaction schemes 5 to 8, $Ar_{22}$, $Ar_{23}$, $L_{21}$ to $L_{23}$, $R_3$ to $R_9$, X, and c to i are as defined in formula 4, formula 1-1, and formula 1-2.

Although illustrative synthesis examples of the compound represented by formula 4 are described above, one skilled in the art will be able to readily understand that all of them are based on a Buchwald-Hartwig cross-coupling reaction, an N-arylation reaction, an H-mont-mediated etherification reaction, a Miyaura borylation reaction, a Suzuki cross-coupling reaction, an Intramolecular acid-induced cyclization reaction, a Pd(II)-catalyzed oxidative cyclization reaction, a Grignard reaction, a Heck reaction, a Cyclic Dehydration reaction, an SN; substitution reaction, an $SN_2$ substitution reaction, a Phosphine-mediated reductive cyclization reaction, etc., and the reactions above proceed even when substituents which are defined in formula 4 above, but are not specified in the specific synthesis examples, are bonded.

The compound represented by formula 1 may be one selected from compounds 1-1 to 1-16, but is not limited thereto.

In the organic electroluminescent device according to the present disclosure, the first electrode and the second electrode may each be formed with a transmissive conductive material, a transflective conductive material, or a reflective conductive material. The organic electroluminescent device may be a top emission type, a bottom emission type, or both-sides emission type according to the kinds of the material forming the first electrode and the second electrode.

In addition, the hole injection layer may be further doped with a p-dopant, and the electron injection layer may be further doped with an n-dopant.

In the organic electroluminescent device according to the present disclosure, the organic layer may further comprise at least one compound selected from the group consisting of arylamine-based compounds and styrylarylamine-based compounds. In addition, in the organic electroluminescent device of the present disclosure, the organic layer may further comprise at least one metal selected from the group consisting of metals of Group 1, metals of Group 2, transition metals of the $4^{th}$ period, transition metals of the $5^{th}$ period, lanthanides and organic metals of d-transition elements of the Periodic Table, or at least one complex compound comprising said metal.

The organic electroluminescent device of the present disclosure may emit white light by further including at least one light-emitting layer containing a blue, red, or green light-emitting compound, which is known in the art, besides the compound of the present disclosure. In addition, it may further include a yellow or orange light-emitting layer, if necessary.

In the organic electroluminescent device of the present disclosure, at least one layer selected from a chalcogenide layer, a metal halide layer and a metal oxide layer (hereinafter, "a surface layer") may be preferably placed on an inner surface(s) of one or both electrodes. Specifically, a chalcogenide (including oxides) layer of silicon or aluminum is preferably placed on an anode surface of an electroluminescent medium layer, and a metal halide layer or a metal oxide layer is preferably placed on a cathode surface of an electroluminescent medium layer. The surface layer may provide operation stability for the organic electroluminescent device. Preferably, the chalcogenide includes $SiO_X$ ($1 \leq X \leq 2$), $AlO_X$ ($1 \leq X \leq 1.5$), SiON, SiAlON, etc.; the metal halide includes LiF, $MgF_2$, $CaF_2$, a rare earth metal fluoride, etc.; and the metal oxide includes $Cs_2O$, $Li_2O$, MgO, SrO, BaO, CaO, etc.

A hole injection layer, a hole transport layer, or an electron blocking layer, or a combination thereof may be used between the anode and the light-emitting layer. The hole injection layer may be multilayers in order to lower the hole injection barrier (or hole injection voltage) from the anode to the hole transport layer or the electron blocking layer, wherein each of the multilayers may use two compounds simultaneously. The hole transport layer or the electron blocking layer may also be multilayers.

An electron buffer layer, a hole blocking layer, an electron transport layer, an electron transport auxiliary layer, or an electron injection layer, or a combination thereof can be used between the light-emitting layer and the cathode. The electron buffer layer may be multilayers in order to control the injection of the electron and improve the interfacial properties between the light-emitting layer and the electron injection layer, wherein each of the multilayers may use two compounds simultaneously. The hole blocking layer or the electron transport layer may also be multilayers, wherein each of the multilayers may use a plurality of compounds.

The light-emitting auxiliary layer may be placed between the anode and the light-emitting layer, or between the cathode and the light-emitting layer. When the light-emitting auxiliary layer is placed between the anode and the light-emitting layer, it can be used for promoting the hole injection and/or the hole transport, or for preventing the overflow of electrons. When the light-emitting auxiliary layer is placed between the cathode and the light-emitting layer, it can be used for promoting the electron injection and/or the electron transport, or for preventing the overflow of holes. In addition, the hole auxiliary layer may be placed between the hole transport layer (or hole injection layer) and the light-emitting layer, and may be effective to promote or block the hole transport rate (or the hole injection rate), thereby enabling the charge balance to be controlled. Further, the electron blocking layer may be placed between the hole transport layer (or hole injection layer) and the light-emitting layer, and may block overflowing electrons from the light-emitting layer and confine the excitons in the light-emitting layer to prevent light leakage. When an organic electroluminescent device includes two or more hole transport layers, the hole transport layer, which is further included, may be used as a hole auxiliary layer or an electron blocking layer. The hole auxillary layer and the electron blocking layer may have an effect of improving the efficiency and/or the lifespan of the organic electroluminescent device.

In the organic electroluminescent device of the present disclosure, a mixed region of an electron transport compound and a reductive dopant, or a mixed region of a hole transport compound and an oxidative dopant is preferably placed on at least one surface of a pair of electrodes. In this case, the electron transport compound is reduced to an anion, and thus it becomes easier to inject and transport electrons from the mixed region to an electroluminescent medium. Further, the hole transport compound is oxidized to a cation, and thus it becomes easier to inject and transport holes from the mixed region to the electroluminescent medium. Preferably, the oxidative dopant includes various Lewis acids and acceptor compounds; and the reductive dopant includes alkali metals, alkali metal compounds, alkaline earth metals, rare-earth metals, and mixtures thereof. A reductive dopant layer may be employed as a charge-generating layer to produce an organic electroluminescent device having two or more light-emitting layers, which emits white light.

An organic electroluminescent material according to one embodiment of the present disclosure may be used as light-emitting materials for a white organic light-emitting device. The white organic light-emitting device has been suggested to have various structures such as a parallel arrangement (side-by-side) method, a stacking method, or color conversion material (CCM) method, etc., according to the arrangement of R (red), G (green), B (blue), or YG (yellowish green) light-emitting units. In addition, the organic electroluminescent material according to one embodiment of the present disclosure may also be applied to the organic electroluminescent device comprising a quantum dot (QD).

In order to form each layer of the organic electroluminescent device of the present disclosure, dry film-forming methods such as vacuum evaporation, sputtering, plasma, ion plating, etc., or wet film-forming methods such as spin coating, dip coating, flow coating, etc., can be used. The first and second host compounds of the present disclosure may be co-evaporated or mixture-evaporated to form a film.

When using a wet film-forming method, a thin film can be formed by dissolving or diffusing the materials forming each layer into any suitable solvent such as ethanol, chloroform, tetrahydrofuran, dioxane, etc. The solvent is not particularly limited as long as the material constituting each layer is soluble or dispersible in the solvents, which do not cause any problems in forming a film.

It is possible to produce a display system, e.g., a display system for smartphones, tablets, notebooks, PCs, TVs, or cars, or a lighting system, e.g., an outdoor or indoor lighting system, by using the organic electroluminescent device of the present disclosure.

Hereinafter, the preparation method of the compound of the present disclosure, and the properties thereof will be explained in detail with reference to the representative compounds of the present disclosure. However, the present disclosure is not limited to the following examples.

Example 1: Preparation of Compound 1-3

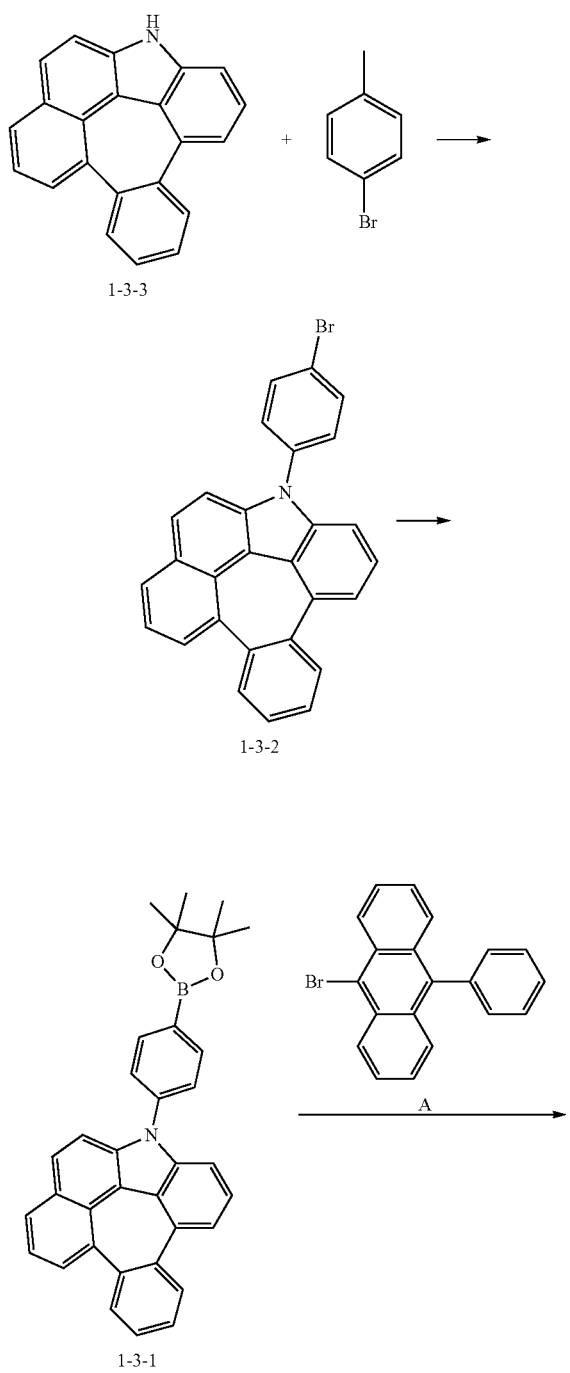

-continued

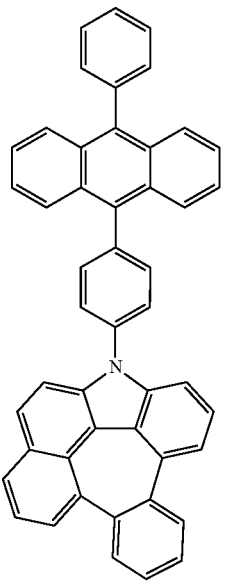

1-3

| Compound | MW | Tg | M.P. |
|---|---|---|---|
| 1-3 | 619.77 | 169.72° C. | 319.6° C. |

Example 2: Preparation of Compound 2-2

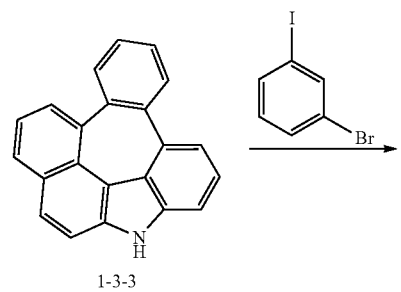

1-3-3

Synthesis of Compound 1-3-2

Compound 1-3-3 (10 g, 34.3 mmol), 1-bromo-4-iodobenzene (24.3 g, 85.8 mmol), copper(I) iodide (3.27 g, 17.2 mmol), ethylenediamine (2.06 g, 34.3 mmol), and potassium phosphate (21.9 g, 103 mmol) were introduced into toluene (170 mL) in a flask and dissolved, and the mixture was refluxed for 2 hours. After completion of the reaction, the reaction mixture was cooled to room temperature and distilled water was added thereto. After extracting with ethyl acetate, the residue was dried with magnesium sulfate. The residue was distilled under reduced pressure and separated by column chromatography to obtain compound 1-3-2 (13.2 g, yield: 86.2%).

Synthesis of Compound 1-3-1

Compound 1-3-2 (13.2 g, 29.6 mmol), bis(pinacolato) diboron (9.76 g, 38.4 mmol), bis (triphenylphosphine) palladium (II) dichloride (830 mg, 1.18 mmol), and potassium acetate (12.8 g, 130 mmol) were introduced into 1,4-dioxane (295 mL) in a flask and dissolved, and the mixture was refluxed at 120° C. for 24 hours. After completion of the reaction, an organic layer was separated with ethyl acetate, and the residual moisture was removed with magnesium sulfate. The residue was separated by column chromatography to obtain compound 1-3-1 (9.4 g, yield: 64.4%).

Synthesis of Compound 1-3

Compound 1-3-1 (9.4 g, 19.1 mmol), compound A (6.35 g, 19.1 mmol), tetrakis(triphenylphosphine) palladium (0) (1.1 g, 0.953 mmol), and potassium carbonate (7.9 g, 57.2 mmol) were introduced into toluene (78 mL), ethanol (23.5 mL), and water (23.5 mL) in a flask and dissolved, and the mixture was refluxed at 120° C. for 24 hours. After completion of the reaction, an organic layer was separated with ethyl acetate, and the residual moisture was removed with magnesium sulfate. The residue was separated by column chromatography to obtain compound 1-3 (2.7 g, 4.36 mmol).

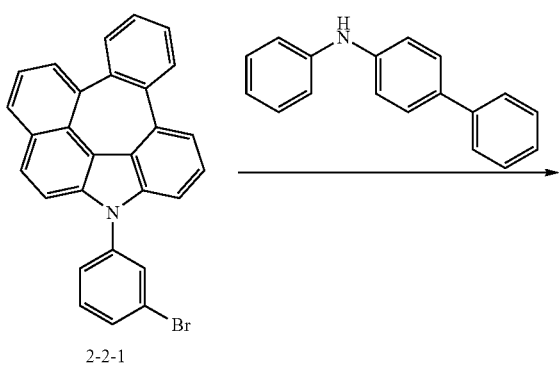

2-2-1

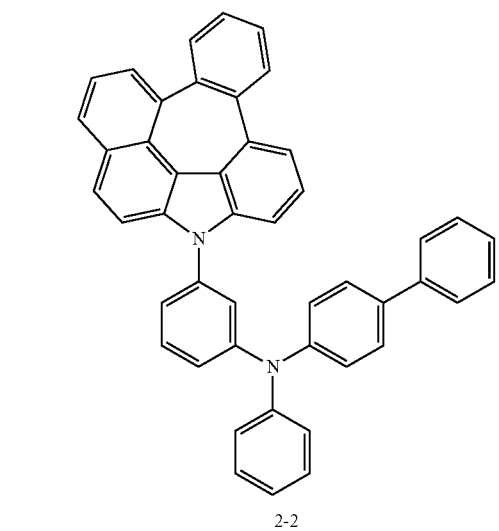

2-2

Synthesis of Compound 2-2-1

Compound 1-3-3 (15.0 g, 51.5 mmol), 1-bromo-3-iodobenzene (29.3 g, 103 mmol), copper(I) iodide (4.9 g, 25.8 mmol), ethylenediamine (7.0 mL, 103 mmol), and potassium phosphate (27.5 g, 129 mmol) were introduced into toluene (250 mL) in a flask and dissolved, and the mixture was stirred under reflux for 4 hours. After completion of the reaction, the reaction mixture was cooled to room temperature and filtered with a silica gel. The organic layer was condensed and recrystallized with ethyl acetate to obtain compound 2-2-1 (14.2 g, yield: 62%).

Synthesis of Compound 2-2

Compound 2-2-1 (5.0 g, 11.2 mmol), N-phenyl-[1,1'-biphenyl]-4-amine (3.0 g, 12.3 mmol), tris(dibenzylideneacetone) dipalladium (0) (0.5 g, 0.56 mmol), s-phos (0.46 g, 1.12 mmol), and sodium tert-butoxide (2.7 g. 28 mmol) were introduced into toluene (60 mL) in a flask and dissolved, and the mixture was stirred under reflux for 6 hours. After completion of the reaction, the reaction mixture was cooled to room temperature, stirred at room temperature, and methanol was added thereto. The obtained solid was filtered under reduced pressure, and separated by column chromatography to obtain compound 2-2 (2.3 g, yield: 34%).

| Compound | MW | Tg | M.P. |
|---|---|---|---|
| 2-2 | 610.8 | 112.31° C. | 132° C. |

Example 3: Preparation of Compound 2-3

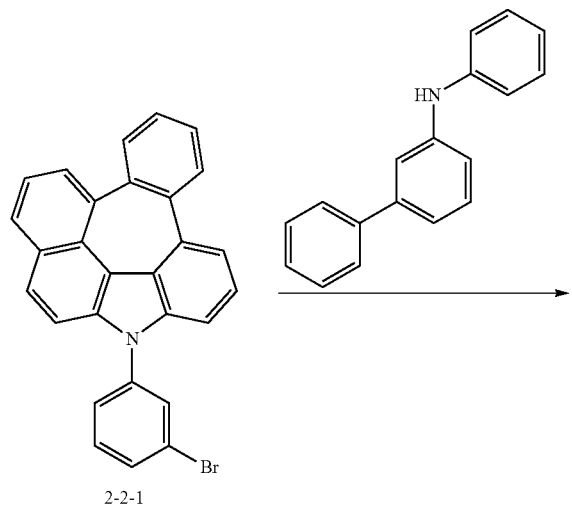

2-2-1

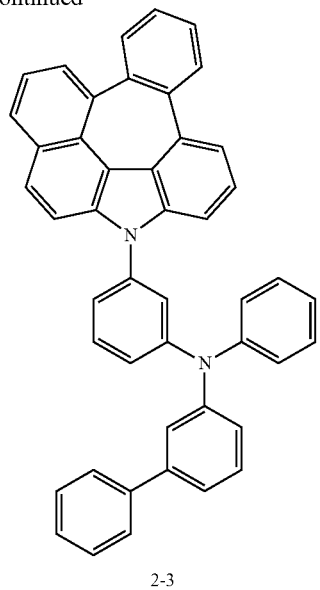

2-3

Compound 2-2-1 (14.0 g, 31.4 mmol). N-phenyl-[1,1'-biphenyl]-3-amine (7.78 g, 31.7 mmol), tris(dibenzylideneacetone) dipalladium (0) (1.44 g, 1.57 mmol), tri-tert-butylphosphine (635 mg, 3.14 mmol), and sodium tert-butoxide (6.04 g, 62.8 mmol) were introduced into toluene (160 mL) in a flask and dissolved, and the mixture was stirred under reflux for 2 hours. After completion of the reaction, the reaction mixture was cooled to room temperature, and extracted with distilled water and ethyl acetate. The organic layer was distilled under reduced pressure, and separated by column chromatography to obtain compound 2-3 (14.6 g, yield: 76%).

| Compound | MW | Tg | M.P. |
|---|---|---|---|
| 2-3 | 610.7 | 103.6° C. | 141° C. |

Device Example 1: Producing an OLED Deposited with the Organic Electroluminescent Compound According to the Present Disclosure An OLED according to the present disclosure was produced. A transparent electrode indium tin oxide (ITO) thin film (10Ω/sq) on a glass substrate for an OLED (GEOMATEC CO., LTD., Japan) was subjected to an ultrasonic washing with acetone, ethanol, and distilled water, sequentially, and then was stored in isopropyl alcohol. The ITO substrate was then mounted on a substrate holder of a vacuum vapor deposition apparatus. Compound HT was introduced into a cell of the vacuum vapor deposition apparatus, and compound HI was introduced into another cell of the vacuum vapor deposition apparatus. The two materials were evaporated at different rates, and compound HI was deposited in a doping amount of 3 wt % based on the total amount of compound HT and compound HI to form a hole injection layer having a thickness of 10 nm on the ITO substrate. Next, compound HT was deposited on the hole injection layer to form a first hole transport layer having a thickness of 75 nm. Compound HT was deposited on the first hole transport layer to form a second hole transport layer having a thickness of 5 nm. After forming the hole injection layer and the hole transport layers, a light-emitting layer was formed thereon as follows: Compound 1-3 was introduced into one cell of the vacuum vapor depositing apparatus as a host of the light-emitting layer, and compound BD was introduced into another cell. The two materials were evaporated at different rates, and respectively deposited in a doping amount of 2 wt % based on the total amount of the host and dopant to form a light-emitting layer having a thickness of 20 nm on the second hole transport layer. Subsequently, compound ET-1 was deposited as a hole blocking layer in a thickness of 5 nm. Next, in two other cells compound ET-2 and compound EI-1 were evaporated at a rate of 1:1 (weight ratio) to deposit an electron transport layer having a thickness of 30 nm on the hole blocking layer. After depositing compound EI-1 as an electron injection layer having a thickness of 2 nm, an Al cathode having a thickness of 80 nm was deposited by another vacuum vapor deposition apparatus to produce an OLED.

As a result, the driving voltage obtained at a luminance of 1,000 nit was 3.2 V, the power efficiency was 5.9 lm/W, and the minimum time taken for luminance to decrease from 100% to 95% was 31.1 hours.

Comparative Example: Producing an OLED Comprising a Conventional Compound

An OLED was produced in the same manner as in Device Example 1, except that compound BH-2 was used as the host of the light-emitting layer.

As a result, the driving voltage obtained at a luminance of 1,000 nit was 4.1 V, the power efficiency was 5.9 lm/W, and the minimum time taken for luminance to decrease from 100% to 95% was 14.6 hours.

As can be seen from the result above, it is verified that the OLED comprising the organic electroluminescent compound according to the present disclosure as a host material can significantly lower the driving voltage and have remarkably improved lifetime properties compared to the OLED using a conventional compound.

Device Example 2: Producing an OLED Deposited with the Organic Electroluminescent Compound According to the Present Disclosure An OLED was produced in the same manner as in Device Example 1, except that compound 2-2 was used instead of compound HT as the second hole transport material.

As a result, the driving voltage obtained at a luminance of 1,000 nit was 3.2 V, and the power efficiency was 6.9 lm/W.

Device Example 3: Producing an OLED Deposited with the Organic Electroluminescent Compound According to the Present Disclosure An OLED was produced in the same manner as in Device Example 1, except that compound 2-3 was used instead of compound HT as the second hole transport material.

As a result, the driving voltage obtained at a luminance of 1,000 nit was 3.2 V, and the power efficiency was 6.9 lm/W.

As can be seen from the result above, it is verified that the OLEDs comprising the organic electroluminescent compound according to the present disclosure as a second hole transport material and a host material can significantly lower the driving voltage and have remarkably improved power efficiency properties compared to the OLED using a conventional compound. High power efficiency in display implementation can represent a higher performance display by implementing an organic electroluminescent device with lower power consumption.

TABLE 3

Organic Electroluminescent Material Used in the Device Examples and the Comparative Example

| | |
|---|---|
| Hole Injection Layer/ Hole Transport Layer | 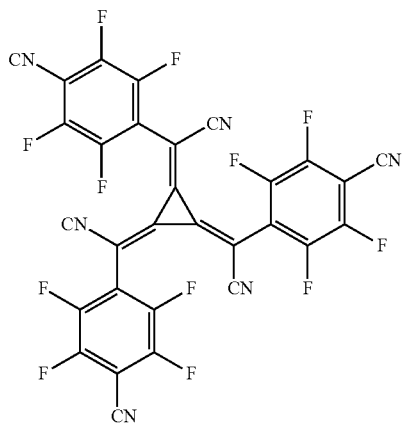 HI |

TABLE 3-continued
Organic Electroluminescent Material Used in
the Device Examples and the Comparative Example
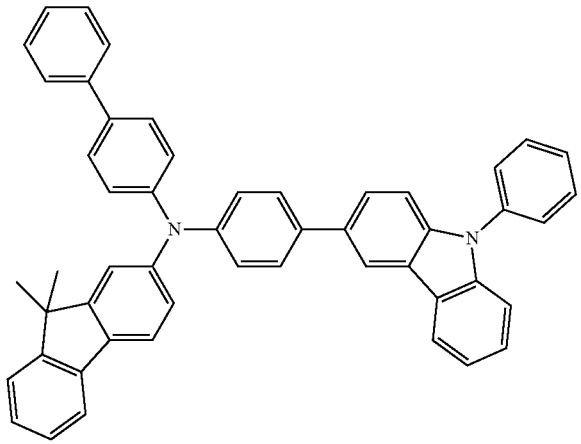 [SMILES: CC1(C)c2ccccc2-c2ccc(N(c3ccc(-c4ccccc4)cc3)c3ccc(-c4ccc5c(c4)c4ccccc4n5-c4ccccc4)cc3)cc21]
HT
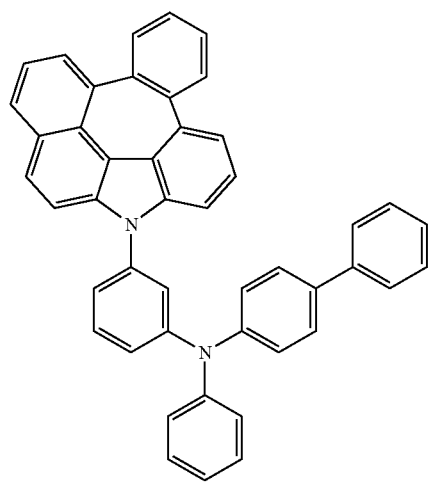 [SMILES: c1ccc(-c2ccc(N(c3ccccc3)c3cccc(-n4c5cccc6c5c5c7c(cccc7ccc54)-c4ccccc4-6)c3)cc2)cc1]
2-2
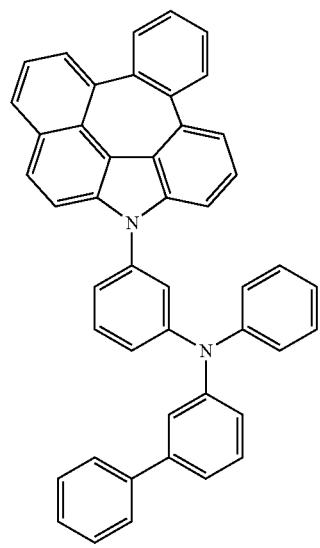 [SMILES: c1ccc(-c2cccc(N(c3ccccc3)c3cccc(-n4c5cccc6c5c5c7c(cccc7ccc54)-c4ccccc4-6)c3)c2)cc1]
2-3

TABLE 3-continued
Organic Electroluminescent Material Used in
the Device Examples and the Comparative Example
Light-
Emitting
Layer
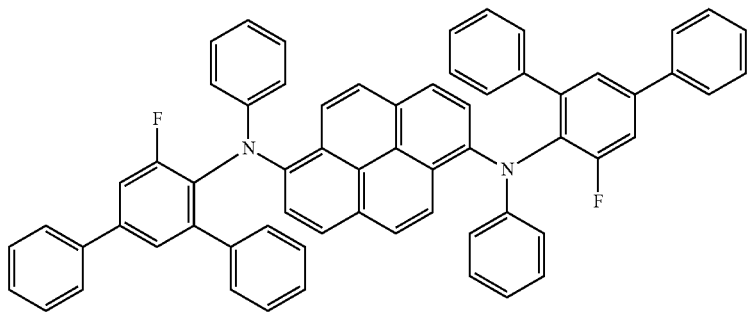 [SMILES: Fc1cc(-c2ccccc2)cc(-c2ccccc2)c1N(c1ccccc1)c1ccc2ccc3c(N(c4ccccc4)c4c(F)cc(-c5ccccc5)cc4-c4ccccc4)ccc4ccc1c2c43]
BD
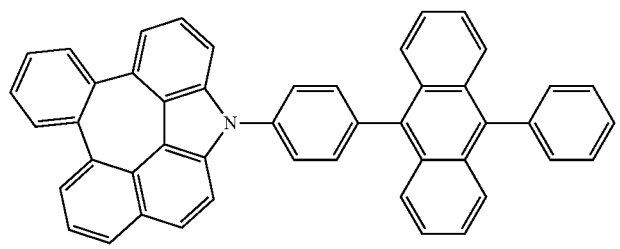 [SMILES: c1ccc(-c2c3ccccc3c(-c3ccc(-n4c5cccc6c5c5c7c(cccc7ccc54)-c4ccccc4-6)cc3)c3ccccc23)cc1]
1-3
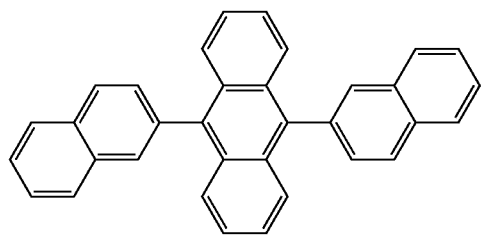 [SMILES: c1ccc2cc(-c3c4ccccc4c(-c4ccc5ccccc5c4)c4ccccc34)ccc2c1]
BH-2
Electron
Transport
Layer/
Electron
Injection
Layer
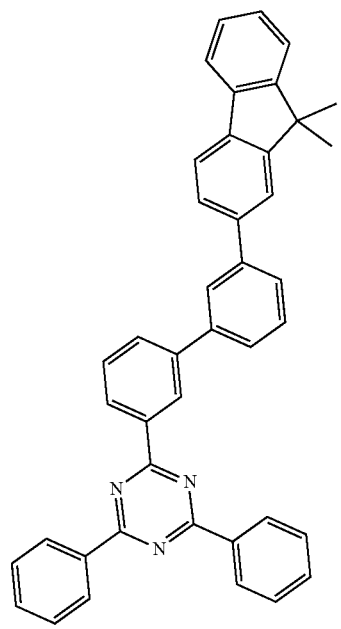 [SMILES: CC1(C)c2ccccc2-c2ccc(-c3cccc(-c4cccc(-c5nc(-c6ccccc6)nc(-c6ccccc6)n5)c4)c3)cc21]

TABLE 3-continued

Organic Electroluminescent Material Used in
the Device Examples and the Comparative Example

ET-1

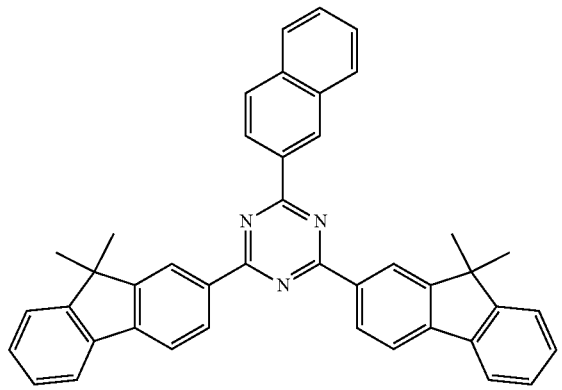 [SMILES: CC1(C)c2ccccc2-c2ccc(-c3nc(-c4ccc5c(c4)C(C)(C)c4ccccc4-5)nc(-c4ccc5ccccc5c4)n3)cc21]

ET-2

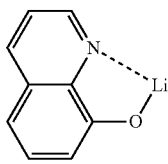

EI-1

The invention claimed is:

1. An organic electroluminescent compound represented by the following formula 1:

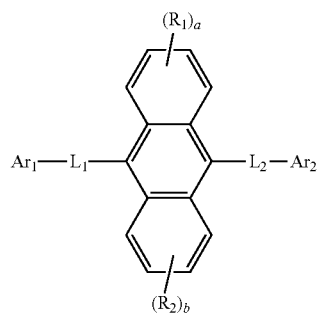

wherein

L₁ and L₂ each independently represent a single bond, a substituted or unsubstituted (C6-C30)arylene, or a substituted or unsubstituted (5- to 30-membered)heteroarylene;

Ar₁ represents a substituted or unsubstituted (C6-C30) aryl, or a substituted or unsubstituted (5- to 30-membered)heteroaryl;

Ar₂ represents the following formula 1-2;

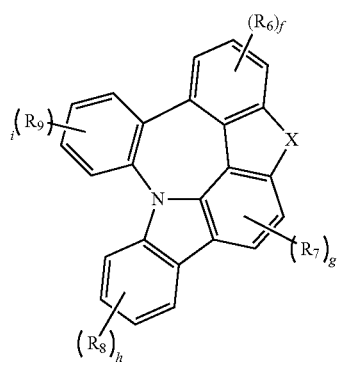

R₁ and R₂ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

R₆ to R₉ each independently represent hydrogen, deuterium, a halogen, a cyano, a substituted or unsubstituted (C1-C30)alkyl, a substituted or unsubstituted (C6-C30)

aryl, or a substituted or unsubstituted (5- to 30-membered)heteroaryl, or may be linked to L₂;

X represents O, S, or N—R₁₁;

R₁₁ represents a substituted or unsubstituted (C1-C30) alkyl, a substituted or unsubstituted (C6-C30)aryl, or a substituted or unsubstituted (5- to 30-membered)heteroaryl, or may be linked to L₂; and a, b, h, and i each independently represent an integer of 1 to 4, f represents an integer of 1 to 3, and g represents an integer of 1 to 2, where if a to i are an integer of 2 or more, each of R₁ to each of R₉ may be the same or different.

2. The organic electroluminescent compound according to claim 1, wherein formula 1 is represented by any one of the following formulas 2-5 to 2-9:

(2-5)

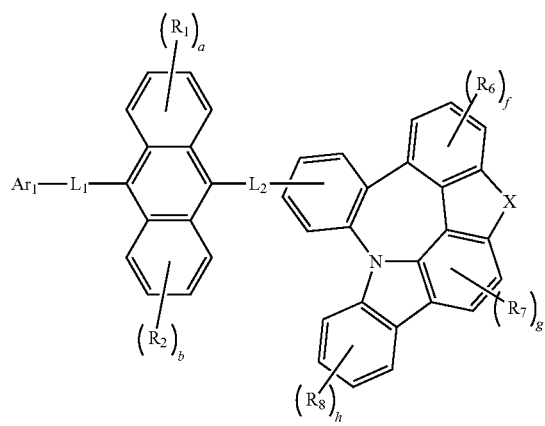

(2-6)

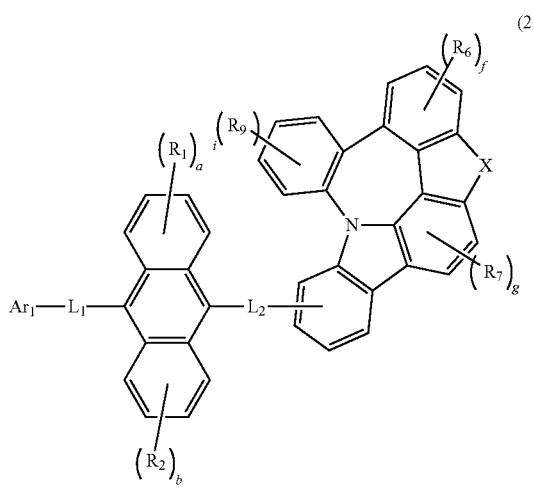

(2-7)

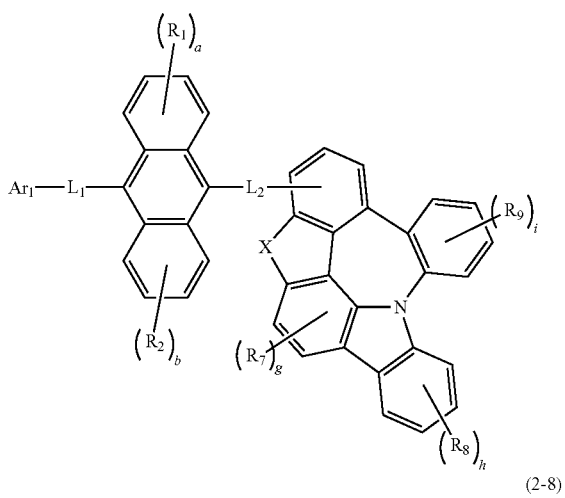

(2-8)

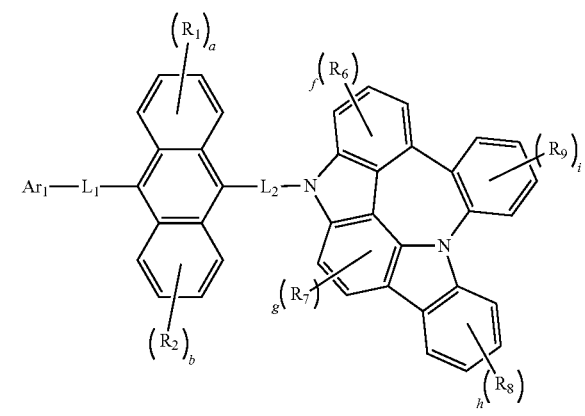

(2-9)

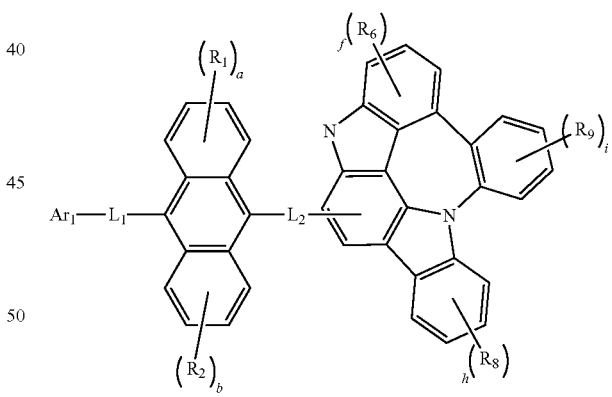

wherein
Ar₁, R₁, R₂, R₆ to R₉, L₁, L₂, X, and a, b, f to i are as defined in claim 1.

3. The organic electroluminescent compound according to claim 1, wherein the substituents of the substituted alkyl, the substituted aryl, the substituted arylene, the substituted heteroaryl, and the substituted heteroarylene in L₁, L₂, R₁, R₂, R₆ to R₉, R₁₁, and Ar₁ each independently are at least one selected from the group consisting of deuterium; a halogen; a cyano; a carboxyl; a nitro; a hydroxyl; a (C1-C30)alkyl; a halo(C1-C30)alkyl; a (C2-C30)alkenyl; a (C2-C30)alkynyl; a (C1-C30)alkoxy; a (C1-C30)alkylthio; a (C3-C30)cycloalkyl; a (C3-C30)cycloalkenyl; a (3- to 7-membered)heterocycloalkyl; a (C6-C30)aryloxy; a (C6-C30)arylthio; a (3- to 30-membered)heteroaryl unsubstituted or substituted with a (C6-C30)aryl(s); a (C6-C30)aryl unsubstituted or substituted with at least one of a (C1-C30)alkyl(s) and a (3- to 30-membered)heteroaryl(s); a tri(C1-C30)alkylsilyl; a tri(C6-C30)arylsilyl; a di(C1-C30)alkyl(C6-C30)arylsilyl; a (C1-C30)alkyldi(C6-C30)arylsilyl; an amino; a mono- or di-(C1-C30)alkylamino; a mono- or di-(C2-C30)alkenylamino; a mono- or di-(C6-C30)arylamino; a mono- or di-(3- to 30-membered)heteroarylamino; a (C1-C30)alkyl(C2-C30)alkenylamino; a (C1-C30)alkyl(C6-C30)arylamino; a (C1-C30)alkyl(3- to 30-membered)heteroarylamino; a (C2-C30)alkenyl(C6-C30)arylamino; a (C2-C30)alkenyl(3- to 30-membered)heteroarylamino; a (C6-C30)aryl(3- to 30-membered)heteroarylamino; a (C1-C30)alkylcarbonyl; a (C1-C30)alkoxycarbonyl; a (C6-C30)arylcarbonyl; a di(C6-C30)arylboronyl; a di(C1-C30)alkylboronyl; a (C1-C30)alkyl(C6-C30)arylboronyl; a (C6-C30)aryl(C1-C30)alkyl; and a (C1-C30)alkyl(C6-C30)aryl.

4. The organic electroluminescent compound according to claim 1, wherein the compound represented by formula 1 is selected from the following compounds:

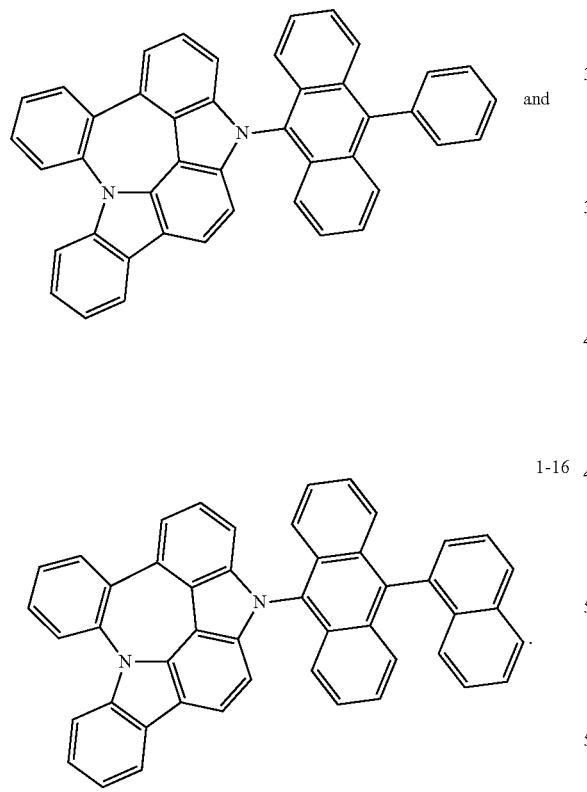

1-15 and 1-16

5. An organic electroluminescent device comprising a first electrode; a second electrode; and a plurality of organic layers comprising a light-emitting layer between the first electrode and the second electrode, wherein at least two layers of the organic layers comprise one or more compounds represented by the following formula 3-2:

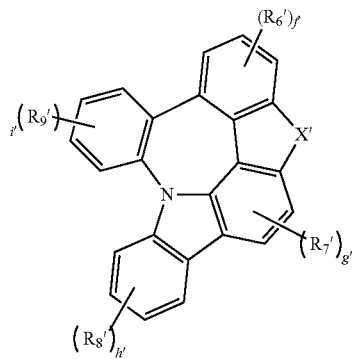

(3-2)

wherein $R_6'$ to $R_9'$ each independently represent hydrogen, deuterium, a halogen, a cyano, a substituted or unsubstituted (C1-C30)alkyl, a substituted or unsubstituted (C6-C60)aryl, a substituted or unsubstituted (3- to 60-membered)heteroaryl, a substituted or unsubstituted (C3-C30)cycloalkyl, a fused ring group of a substituted or unsubstituted (C3-C30) aliphatic ring(s) and a substituted or unsubstituted (C6-C30) aromatic ring(s), a substituted or unsubstituted (C2-C30)alkenyl, a substituted or unsubstituted (C2-C30)alkynyl, a substituted or unsubstituted (C1-C30)alkoxy, a substituted or unsubstituted (C6-C30)aryloxy, a substituted or unsubstituted mono- or di-(C1-C30)alkylamino, a substituted or unsubstituted mono- or di-(C2-C30)alkenylamino, a substituted or unsubstituted mono- or di-(C6-C30)arylamino, a substituted or unsubstituted mono- or di-(3- to 30-membered)heteroarylamino, a substituted or unsubstituted (C1-C30)alkyl(C2-C30)alkenylamino, a substituted or unsubstituted (C1-C30)alkyl(C6-C30)arylamino, a substituted or unsubstituted (C1-C30)alkyl(3- to 30-membered)heteroarylamino, a substituted or unsubstituted (C2-C30)alkenyl(C6-C30)arylamino, a substituted or unsubstituted (C2-C30)alkenyl(3- to 30-membered)heteroarylamino, or a substituted or unsubstituted (C6-C30)aryl(3- to 30-membered)heteroarylamino, or may be linked to an adjacent substituent to form a ring(s);

X' represents O, S, or N—$R_{11}'$;

$R_{11}'$ represents -$L_{11}$-$Ar_3$;

$L_{11}$ represents a single bond, a substituted or unsubstituted (C6-C30)arylene, or a substituted or unsubstituted (5- to 30-membered)heteroarylene;

$Ar_3$ represents hydrogen, a substituted or unsubstituted (C1-C30)alkyl, a substituted or unsubstituted (C6-C30)aryl, a substituted or unsubstituted (5- to 30-membered) heteroaryl, a substituted or unsubstituted mono- or di-(C6-C60)arylamino, a substituted or unsubstituted mono- or di-(3- to 60-membered)heteroarylamino, or a substituted or unsubstituted (C6-C60)aryl(3- to 60-membered)heteroarylamino; and h' and i' each independently represent an integer of 1 to 4, f' represents an integer of 1 to 3, and g' represents an integer of 1 to 2, where if f' to i' are an integer of 2 or more, each of $R_6'$ to each of $R_9'$ may be the same or different;

wherein the compound represented by formula 3-2 comprised in at least one organic layer is represented by formula 1, and the compound represented by formula 3-2 comprised in at least another organic layer is represented by formula 4:

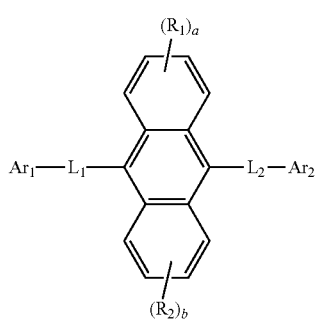

(1)

wherein

L₁ and L₂ each independently represent a single bond, a substituted or unsubstituted (C6-C30)arylene, or a substituted or unsubstituted (5- to 30-membered)heteroarylene;

Ar₁ represents a substituted or unsubstituted (C6-C30) aryl, or a substituted or unsubstituted (5- to 30-membered)heteroaryl;

Ar₂ represents the following formula 1-2;

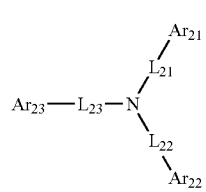

(4)

wherein at least one of $Ar_{21}$ to $Ar_{23}$ each independently represent the following formula 1-2, and the other(s) of $Ar_{21}$ to $Ar_{23}$ each independently represent a substituted or unsubstituted (C6-C30)aryl, or a substituted or unsubstituted (5- to 30-membered)heteroaryl;

$L_{21}$ to $L_{23}$ each independently represent a single bond, a substituted or unsubstituted (C6-C30)arylene, or a substituted or unsubstituted (5- to 30-membered)heteroarylene;

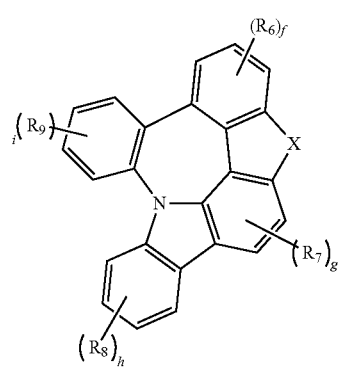

(1-2)

R₁ and R₂ each independently represent hydrogen, deuterium, a halogen, a cyano, a substituted or unsubstituted (C1-C30)alkyl, a substituted or unsubstituted (C6-C30)aryl, or a substituted or unsubstituted (5- to 30-membered)heteroaryl;

R₆ to R₉ each independently represent hydrogen, deuterium, a halogen, a cyano, a substituted or unsubstituted (C1-C30)alkyl, a substituted or unsubstituted (C6-C30) aryl, or a substituted or unsubstituted (5- to 30-membered)heteroaryl, or may be linked to L₂, or also may be linked to one or more of $L_{21}$ to $L_{23}$;

X represents O, S, or N—R₁₁;

R₁₁ represents a substituted or unsubstituted (C1-C30) alkyl, a substituted or unsubstituted (C6-C30)aryl, or a substituted or unsubstituted (5- to 30-membered)heteroaryl, or may be linked to L₂, or also may be linked to one or more of $L_{21}$ to $L_{23}$; and a, b, h, and i each independently represent an integer of 1 to 4, f represents an integer of 1 to 3, and g represents an integer of 1 to 2, where if a to i are an integer of 2 or more, each of R₆ to each of R₉ may be the same or different.

6. The organic electroluminescent device according to claim 5, wherein the compound represented by formula 4 is selected from the following compounds:

2-12

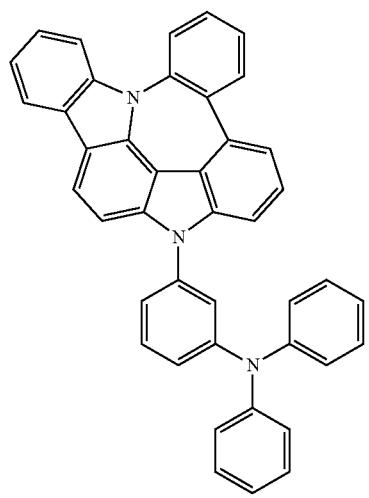

2-13

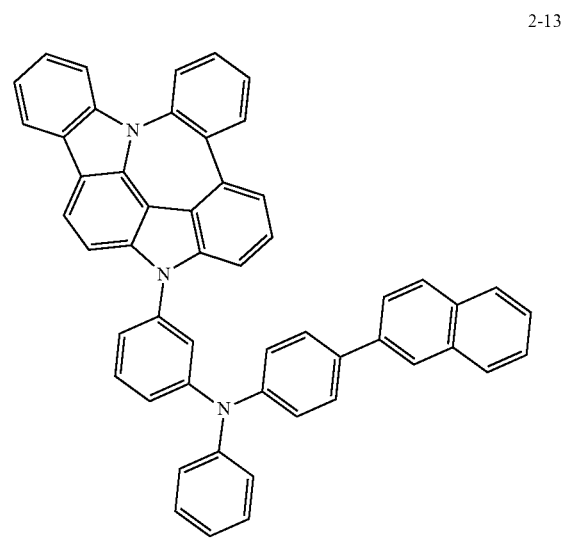

2-14
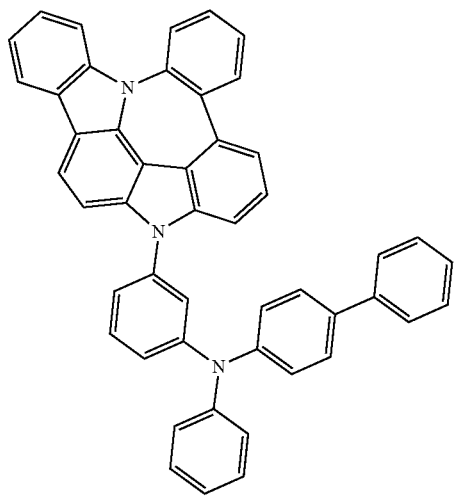
2-15
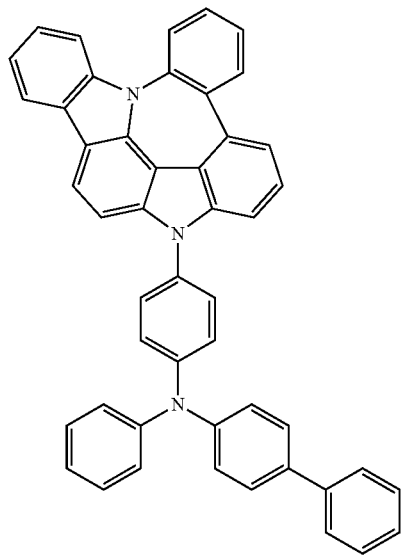
2-16
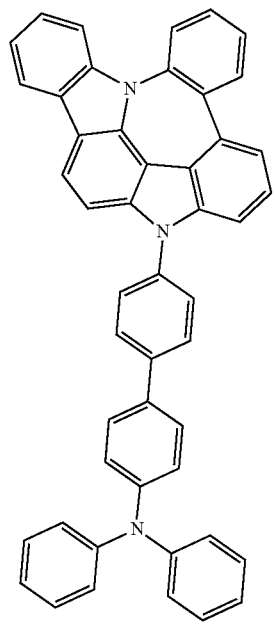
2-17
2-18
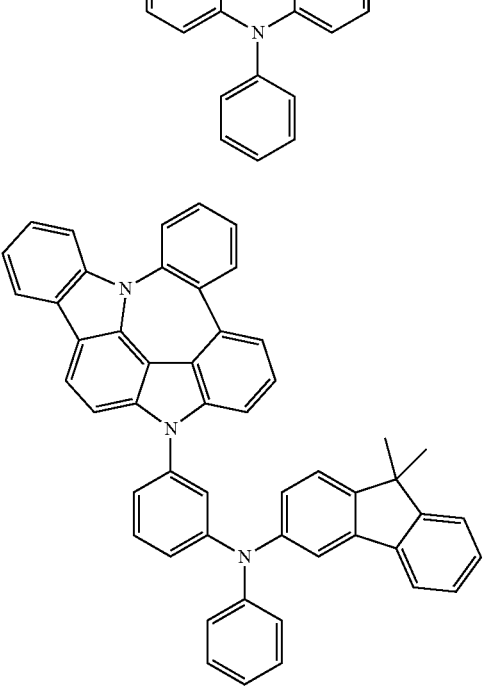

-continued
2-23
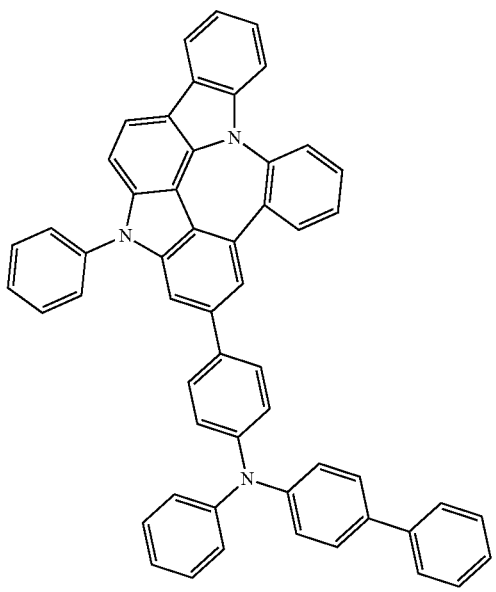
and
2-24
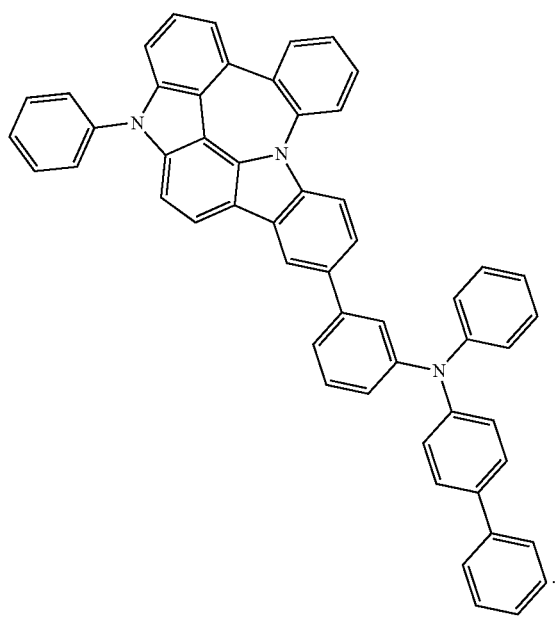
7. The organic electroluminescent device according to claim 5, wherein the compound represented by formula 1 is selected from the following compounds:
1-15
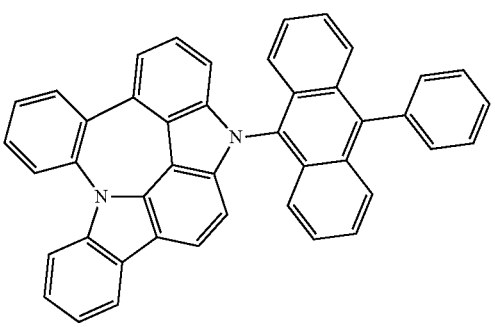
and
1-16
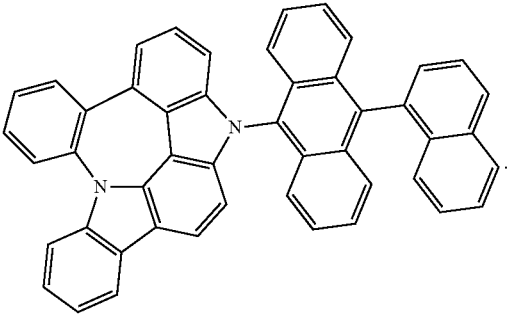
\* \* \* \* \*